(12) United States Patent
Harris et al.

(10) Patent No.: US 7,166,616 B2
(45) Date of Patent: Jan. 23, 2007

(54) SUBSTITUTED ALKANOIC ACIDS

(75) Inventors: Neil Victor Harris, West Malling (GB); Garry Fenton, West Malling (GB)

(73) Assignee: Aventis Pharma Limited, West Malling (GB)

( * ) Notice: Subject to any disclaimer, the term of this patent is extended or adjusted under 35 U.S.C. 154(b) by 319 days.

(21) Appl. No.: 10/427,598

(22) Filed: May 1, 2003

(65) Prior Publication Data

US 2004/0006056 A1  Jan. 8, 2004

Related U.S. Application Data

(63) Continuation of application No. PCT/GB01/04864, filed on Nov. 2, 2001.

(60) Provisional application No. 60/335,590, filed on Oct. 24, 2001, provisional application No. 60/256,170, filed on Dec. 13, 2000.

(30) Foreign Application Priority Data

Nov. 4, 2000 (GB) .................................. 0027024.9
Oct. 12, 2001 (GB) .................................. 0124528.1

(51) Int. Cl.
*C07D 263/58* (2006.01)
*C07D 261/02* (2006.01)
*A61K 31/423* (2006.01)
*A61K 31/445* (2006.01)

(52) U.S. Cl. ...................... 514/321; 514/375; 548/222; 546/198

(58) Field of Classification Search ................ 548/222; 514/375, 321; 546/198
See application file for complete search history.

(56) References Cited

FOREIGN PATENT DOCUMENTS

| WO | WO 99/33789 | 7/1999 |
| WO | WO 00/15612 | 3/2000 |
| WO | WO 02/36553 | 5/2002 |

*Primary Examiner*—Joseph K. McKane
*Assistant Examiner*—Rebecca Anderson
(74) *Attorney, Agent, or Firm*—Ronald G. Ort

(57) ABSTRACT

The invention is directed to physiologically active compounds of general formula (I):

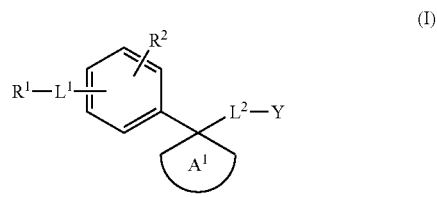

wherein:

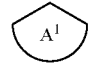

represents (i) a saturated 3 to 6 membered carbocycle, optionally substituted by one or more alkyl groups, (ii) indanyl or (iii) a saturated 4 to 6 membered heterocyclic ring;
$R^1$ represents $R^3Z^1$-Het- or $R^4N(R^5)$—C(=O)—NH—$Ar^1$—;
$L^1$ represents an —$R^6$—$R^7$— linkage;
$R^2$ represents hydrogen, halogen, lower alkyl or lower alkoxy;
$L^2$ represents an alkylene linkage;
Y is carboxy or an acid bioisostere;
and their corresponding N-oxides or prodrugs, and pharmaceutically acceptable salts and solvates of such compounds and their corresponding N-oxides or prodrugs.

Such compounds have valuable pharmaceutical properties, in particular the ability to regulate the interaction of VCAM-1 and fibronectin with the integrin VLA-4 (α4β1).

19 Claims, No Drawings

SUBSTITUTED ALKANOIC ACIDS

This application is a continuation of PCT/GB01/04864, filed Nov. 2, 2001, which claims priority from GB Application No. 0027024.9, filed Nov. 4, 2000, U.S. Provisional Application No. 60/256,170, filed Dec. 13, 2000, GB Application No. 0124528.1, filed Oct. 12, 2001, and U.S. Provisional Application No. 60/335,590, filed Oct. 24, 2001; all of these applications incorporated herein by reference.

This invention is directed to substituted phenyl-cycloalkyl-(and heterocycloalkyl)alkanoic acids, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extracellular matrix interactions are mediated by protein ligands (e.g. fibronectin, VCAM-1 and vitronectin) and their integrin receptors [e.g. $\alpha5\beta1$ (VLA-5), $\alpha4\beta1$ (VLA-4) and $\alpha V\beta3$]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen, fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called $\alpha$ and $\beta$. There are at least fifteen different $\alpha$-subunits ($\alpha1–\alpha9$, $\alpha$-L, $\alpha$-M, $\alpha$-X, $\alpha$-IIb, $\alpha$-V and $\alpha$-E) and at least seven different $\beta$ ($\beta1–\beta7$) subunits. The integrin family can be subdivided into classes based on the $\beta$ subunits, which can be associated with one or more $\alpha$-subunits. The most widely distributed integrins belong to the $\beta1$ class, also known as the very late antigens (VLA). The second class of integrins are leukocyte specific receptors and consist of one of three $\alpha$-subunits ($\alpha$-L, $\alpha$-M or $\alpha$-X) complexed with the $\beta2$ protein. The cytoadhesins $\alpha$-IIb$\beta3$ and $\alpha$-V$\beta3$, constitute the third class of integrins The present invention principally relates to agents which modulate the interaction of the ligand VCAM-1 with its integrin receptor $\alpha4\beta1$ (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin $\alpha4\beta1$ mediates both cell-cell and cell-matrix interactions. Cells expressing $\alpha4\beta1$ bind to the carboxy-terminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-$\gamma$, TNF-$\alpha$, IL-1$\beta$ and IL-4.

Regulation of $\alpha4\beta1$ mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease, multiple sclerosis and stroke, has been accumulated by investigating the role of the peptide CS-1 (the variable region of fibronectin to which $\alpha4\beta1$binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J. Clin. Invest., 1994, 94, pages 655–662). In the oxazalone-sensitised model of inflammation (contact hypersensitivity response) in mice, intravenous administration of anti-$\alpha4$ specific monoclonal antibodies significantly inhibited (50–60% reduction in the ear swelling response) the efferent response (P. L. Chisholm et al. J. Immunol., 1993, 23, pages 682–688). In a sheep model of allergic bronchoconstriction, HP1/2, an anti-$\alpha4$ monoclonal antibody given intravenously or by aerosol, blocked the late response and the development of airway hyperresponsiveness (W. M. Abraham et al. J. Clin. Invest., 1994, 93, pages 776–787). Antibody to the $\alpha4$-integrin has been shown to decrease infarct size in transient focal cerebral ischaemia in rats (K. Becker et al. Stroke, 2001, 32, page 206).

We have now found a novel group of substituted phenyl-cycloalkyl-(and heterocycloalkyl)alkanoic acids which have valuable pharmaceutical properties, in particular the ability to regulate the interaction of VCAM-1 and fibronectin with the integrin VLA-4 ($\alpha4\beta1$).

Thus, in one aspect, the present invention is directed to compounds of general formula (I):

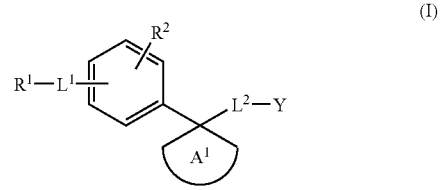

wherein:

represents (i) a saturated 3 to 6 membered carbocycle, optionally substituted by one or more alkyl groups, (ii) indanyl or (iii) a saturated 4 to 6 membered heterocyclic ring;

$R^1$ represents $R^3Z^1$-Het- or $R^4N(R^5)$—C(=O)—NH—Ar$^1$—;

$R^2$ represents hydrogen, halogen, lower alkyl or lower alkoxy;

Het represents a saturated, partially saturated or fully unsaturated 8 to 10 membered bicyclic ring system containing at least one heteroatom selected from O, S or N, optionally substituted by one or more aryl group substituents;

$R^3$ represents optionally substituted aryl or optionally substituted heteroaryl;

$R^4$ represents hydrogen or lower alkyl and $R^5$ represents aryl, arylalkyl, heteroaryl or heteroarylalkyl; or $R^4$ and $R^5$ together with the nitrogen atom to which they are attached form a cyclic amine;

$R^6$ is a direct bond or an alkylene chain, an alkenylene chain or an alkynylene chain;

$R^7$ is a direct bond, cycloalkylene, heterocycloalkylene, aryldiyl, heteroaryldiyl, —C(=$Z^2$)—$NR^8$—, —$NR^8$—C(=$Z^2$)—, —$Z^2$—, —C(=O)—, —C(=$NOR^8$)—, —$NR^8$—, —$NR^8$—C(=$Z^2$)—$NR^8$—, —$SO_2$—$NR^8$—, —$NR^8$—$SO_2$—, —O—C(=O)—, —C(=O)—O—, —$NR^8$—C(=O)—O— or —O—C(=O)—$NR^8$—; or $R^6$ and $R^7$ together represent a direct bond;

$R^8$ represents hydrogen or lower alkyl;

$Ar^1$ represents aryldiyl or heteroaryldiyl;

$L^1$ represents an —$R^6$—$R^7$— linkage;

$L^2$ represents an alkylene linkage;

Y is carboxy or an acid bioisostere;

$Z^1$ represents NH;

$Z^2$ is O or S;

and the corresponding N-oxides, and their prodrugs; and pharmaceutically acceptable salts and solvates (e.g. hydrates) of such compounds and their N-oxides and prodrugs, but excluding compounds where an oxygen, nitrogen or sulfur atom is attached directly to a carbon-carbon multiple bond of an alkenylene or alkynylene residue.

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, page 283 "Bioisosterism In Drug Design"; Yun, Hwahak Sekye, 1993, 33, pages 576–579 "Application Of Bioisosterism To New Drug Design"; Zhao, Huaxue Tongbao, 1995, pages 34–38 "Bioisosteric Replacement And Development Of Lead Compounds In Drug Design"; Graham, Theochem, 1995, 343, pages 105–109 "Theoretical Studies Applied To Drug Design:ab initio Electronic Distributions In Bioisosteres"). Examples of suitable acid bioisosteres include: —C(=O)—NHOH, —C(=O)—$CH_2OH$, —C(=O)—$CH_2SH$, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means a H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably 2 to about 6 carbon atoms, particularly 2 to 4 carbon atoms, in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, hexenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include groups having 1 to 7 carbon atoms such as methoxy, ethoxy, n-propoxy, i-propoxy, n-butoxy, n-pentyloxy, n-hexyloxy and n-heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be straight or branched having 1 to about 4 carbon atoms in the chain. Exemplary alkyl groups include methyl, ethyl, n-propyl, i-propyl, n-butyl, s-butyl, t-butyl, n-pentyl, 3-pentyl, hexyl, heptyl, octyl, nonyl, decyl and dodecyl.

"Alkylene" means an aliphatic bivalent radical derived from a straight or branched alkyl group, in which the alkyl group is as described herein. Preferred alkylene radicals are those in which the alkyl group is $C_{1-3}$alkyl. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-$SO_2$— group in which the alkyl group is as previously described. Preferred alkylsulfonyl groups are those in which the alkyl group is $C_{1-4}$alkyl.

"Alkylsulfonylcarbamoyl" means an alkyl-$SO_2$—NH—C(=O)— group in which the alkyl group is as previously described. Preferred alkylsulfonylcarbamoyl groups are those in which the alkyl group is $C_{1-4}$alkyl.

"Alkylthio" means an alkyl-S— group in which the alkyl group is as previously described. Preferred alkylthio groups are those in which the alkyl group is $C_{1-4}$alkyl.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Preferred alkynylene radicals include radicals have 2 to 3 carbon atoms in the chain. Exemplary alkynylene radicals include ethynylene and propynylene.

"Arroyo" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which a monocyclic aromatic carbocyclic moiety and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyloxy, heteroaroylamino, heteroaryloxy, hydroxy, nitro, trifluoromethyl, $Y^1Y^2N$—, $Y^1Y^2NCO$—, $Y^1Y^2NSO_2$— [where $Y^1$ and $Y^2$ are independently hydrogen, alkenyl, alkyl, aryl, arylalkyl, cycloalkyl, heteroaryl or heteroarylalkyl; or the group —$NY^1Y^2$ may form a cyclic amine], $Y^1Y^2N$—$C_{2-6}$alkylene-$Z^3$— [in which $Z^3$ represents $NR^8$, O, S, SO or $S^2$] and, alkylC(=O)—$Y^1N$—, alkyl$SO_2$—$Y^1N$— or alkyl optionally substituted with aryl, heteroaryl, hydroxy, or $Y^1Y^2N$—.

"Arylalkyl" means an aryl-alkyl-group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryldiyl" means an optionally substituted bivalent radical derived from an aryl group. Exemplary aryldiyl groups include optionally substituted phenylene, naphthylene and indanylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylsulfonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulfur, or nitrogen. Examples of azaheteroaryl groups include benzimidazolyl, imidazolyl, isoquinolinyl, isoxazolyl, pyrazolopyrimidinyl, pyridyl, pyrimidinyl, quinolinyl, quinazolinyl and thiazolyl.

"Azaheteroaryldiyl" means an optionally substituted bivalent radical derived from a heteroaryl group.

"Carbocycle" means a saturated monocyclic ring system of 3 to 6 carbon atoms optionally substituted by alkyl. Exemplary cycloalkyl rings include cyclopropyl, cyclobutyl, cyclopentyl and cyclohexyl.

"Cyclic amine" means a 3 to 8 membered monocyclic cycloalkyl ring system where one of the ring carbon atoms is replaced by nitrogen and which (i) may optionally contain an additional heteroatom selected from O, S or $NY^3$ (where $Y^3$ is hydrogen, alkyl, arylalkyl, and aryl) and (ii) may be fused to additional aryl or heteroaryl ring to form a bicyclic ring system. Exemplary cyclic amines include pyrrolidine, piperidine, morpholine, piperazine, indoline and pyrindoline.

"Cycloalkylene" means a bivalent radical derived from a saturated monocyclic hydrocarbon of about 3 to about 10 carbon atoms by removing a hydrogen atom from each of two different carbon atoms of the ring. Exemplary cycloalkenylene radicals include cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety is as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulfur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a monocyclic heteroaromatic moiety and a cycloalkyl or cycloalkenyl group are fused together to form a cyclic structure (examples of such groups include pyrindanyl groups). Optional substituents include one or more "aryl group substituents" as defined above.

"Heteroarylalkyl" means a heteroaryl-alkyl-group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means a heteroarylalkyl-O— group in which the heteroarylalkyl group is as previously described. Exemplary heteroaryloxy groups include optionally substituted pyridylmethoxy.

"Heteroaryldiyl" means a bivalent radical derived from an aromatic monocyclic or multicyclic organic moiety of about 5 to about 10 ring members in which one or more of the ring members is/are element(s) other than carbon, for example nitrogen, oxygen or sulfur, and optionally substituted by one or more "aryl group substituents" as defined above.

"Heteroaryloxy" means a heteroaryl-O— group in which the heteroaryl group is as previously described. Exemplary heteroaryloxy groups include optionally substituted pyridyloxy.

"Heteroarylsulfonylcarbamoyl" means a heteroaryl-$SO_2$—NH—C(=O)— group in which the heteroaryl group is as previously described.

"Heterocycloalkylene" means a bivalent radical derived from a saturated monocyclic hydrocarbon of about 5 to about 7 atoms, which contains one or more heteroatoms selected from O, S or $NY^{Y4}$ (where $Y^4$ is hydrogen, alkyl, arylalkyl, and aryl) and is optionally substituted by oxo, by removing a hydrogen atom from each of two different carbon atoms of the ring, or when $NY^4$ is NH by removing a hydrogen atom from one carbon atom of the ring and a hydrogen atom from the NH, or when the ring contains two $NY^4$ heteroatoms and $NY^4$ is NH by removing a hydrogen atom from both nitrogen atoms.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group are, for example, acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of formula (I) containing a carboxy group, are for example those described by F. J. Leinweber, Drug Metab. Res., 1987, 18, page 379.

An especially useful class of esters of compounds of formula (I) containing a hydroxy group, may be formed from acid moieties selected from those described by Bundgaard et. al., J. Med. Chem., 1989, 32, pages 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

may particularly represent a saturated 3 to 6 membered carbocycle, optionally substituted by one or more alkyl groups.

is preferably cyclopropyl, cyclobutyl, cyclopentyl or 3,3-dimethylcyclopentyl.

may also particularly represent indanyl.

may also particularly represent a 4 to 6 membered heterocyclic ring in which the heteroatom is selected from O, S, SO$_2$, or NY$^5$ (where Y$^5$ is hydrogen, alkyl, aryl, arylalkyl, —C(=O)—R, —C(=O)—OR or —SO$_2$R and R is alkyl, aryl, arylalkyl, cycloalkyl, cycloalkylalkyl, heteroaryl, heteroarylalkyl, heterocycloalkyl or heterocycloalkylalkyl).

is preferably a 6 membered heterocyclic ring in which the heteroatom is O or NY$^5$ (where Y$^5$ is hydrogen, alkyl, or —C(=O)-alkyl). R$^1$ may particularly represent a group R$^3$Z$^1$-Het- in which R$^3$ is optionally substituted aryl (especially optionally substituted phenyl) or optionally substituted heteroaryl, Z$^1$ is NH and Het is an 8 to 10 membered bicyclic system

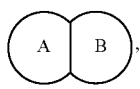

wherein ring

is a 5 or 6 membered heteroaryl ring and ring

is a 5 or 6 membered heteroaryl or a benzene ring, each ring optionally substituted by one or more "aryl group substituents" as defined above, and the two rings are joined together by a carbon-carbon linkage or a carbon-nitrogen linkage.

Ring

may particularly represent a 5 membered heteroaryl ring (especially a 5 membered azaheteroaryl ring), optionally substituted by one or more "aryl group substituents" as defined above.

Ring

may particularly represent a benzene ring, optionally substituted by one or more "aryl group substituents" as defined above.

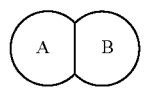

may particularly represent a 9 membered bicyclic system in which rings

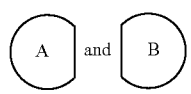

and are as defined just above where the two bridge atoms are carbon.

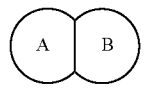

is preferably optionally substituted benzoxazolyl or optionally substituted benzimidazolyl, each (more particularly ring

optionally substituted by one or more "aryl group substituents" as defined above [examples of particular aryl group substituents include lower alkyl (e.g. methyl), lower alkoxy (e.g. methoxy), amino, halogen, hydroxy, lower alkylthio, lower alkylsulfinyl, lower alkylsulfonyl, nitro or trifluoromethyl].

$R^1$ may also particularly represent a group $R^4N(R^5)$—C(=O)—NH—$Ar^1$— in which $R^4$ is hydrogen, $R^5$ is (i) aryl, especially optionally substituted phenyl, where the optional substituent is an "aryl group substituent" as defined above or (ii) optionally substituted pyridyl, especially optionally substituted 2-pyridyl (preferred optional substituents include $C_{1-4}$alkyl and $C_{1-4}$alkoxy, especially methyl and methoxy) and $Ar^1$ is (i) optionally substituted phenylene, such as optionally substituted m- or p-phenylene, preferably optionally substituted p-phenylene, more preferably a 3-substituted p-phenylene (preferred optional substituents include $C_{1-4}$alkyl, $C_{1-4}$alkoxy, $C_{1-4}$alkylthio, $C_{1-4}$alkylsulfinyl and $C_{1-4}$alkylsulfonyl, especially methyl, methoxy, methylthio, methylsulfinyl and methylsulfonyl) or (ii) optionally substituted azaheteroaryldiyl, such as optionally substituted pyridinediyl, preferably a p-pyridinediyl, where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group. $R^5$ is particularly phenyl or ortho substituted phenyl [preferred substituents include $C_{1-4}$alkoxy (e.g. methoxy) or especially $C_{1-4}$alkyl (e.g. methyl)]. $Ar^1$ is preferably optionally substituted phenylene (e.g. p-phenylene), especially where the substituent is $C_{1-4}$alkyl or $C_{1-4}$alkoxy.

$R^2$ may particularly represent hydrogen.

$L^1$ may particularly represent a —$R^6$—$R^7$— linkage where $R^6$ represents a straight or branched $C_{1-6}$alkylene chain, especially a straight or branched $C_{1-4}$alkylene chain (e.g. methylene), and $R^7$ represents —C(=$Z^2$)—$NR^8$—, preferably —C(=O)—$NR^8$—, especially where $R^8$ is hydrogen or lower alkyl (e.g. methyl).

Y may particularly represent carboxy.

$L^2$ may particularly represent an alkylene linkage, especially methylene.

It is to be understood that this invention covers all appropriate combinations of the particular and preferred groupings referred to herein.

A particular group of compounds of the invention are compounds of formula (Ia):

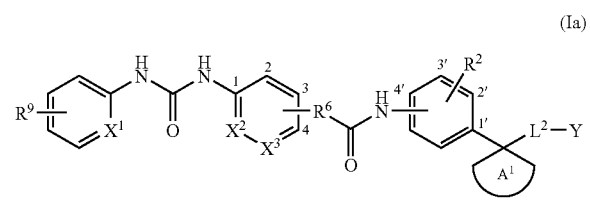

in which

$R^2$, $R^6$, $L^2$ and Y are as hereinbefore defined, $R^9$ is hydrogen, halogen, lower alkyl or lower alkoxy, $X^1$ is $CR^{10}$ (where $R^{10}$ is hydrogen, lower alkyl or lower alkoxy), $X^2$ and $X^3$ independently represent N or $CR^{11}$ (where $R^{11}$ is hydrogen, amino, halogen, hydroxy, lower alkyl, lower alkoxy, lower alkylthio, lower alkylsulfinyl, lower alkylsulfonyl, nitro or trifluoromethyl), and the group containing $R^6$ is attached at the ring 3 or 4 position, and their prodrugs and pharmaceutically acceptable salts, and solvates (e.g. hydrates) of compounds of formula (Ia) and their prodrugs.

Compounds of formula (Ia) in which

represents

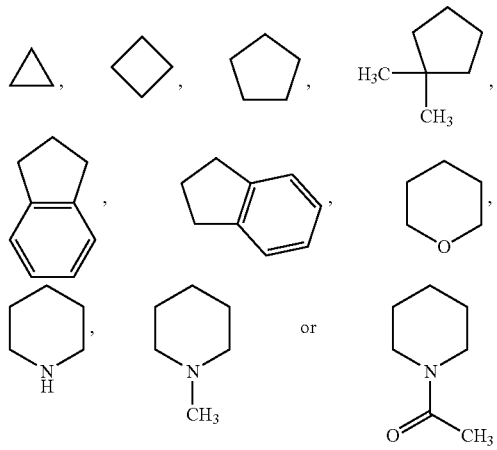

preferred.

Compounds of formula (Ia) in which $R^9$ represents hydrogen are preferred.

Compounds of formula (Ia) in which $X^1$ represents $CR^{10}$ where $R^{10}$ is $C_{1-4}$alkyl (e.g. methyl) are preferred.

Compounds of formula (Ia) in which $X^2$ represents $CR^{11}$, especially where $R^{11}$ is $C_{1-4}$alkoxy (e.g. methoxy) are also preferred.

Compounds of formula (Ia) in which $X^3$ represents CH are also preferred.

Compounds of formula (Ia) in which $R^6$ represents a straight or branched $C_{1-6}$alkylene chain, especially a straight $C_{1-4}$alkylene chain, more especially methylene, are preferred.

Compounds of formula (Ia) in which $R^2$ represents hydrogen are preferred.

Compounds of formula (Ia) in which Y represents carboxy are preferred.

$R^6$ of the group

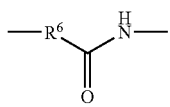

may preferably be attached at the ring 4 position.
The nitrogen atom of the group

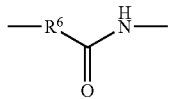

may preferably be attached at the ring 4' position.

A preferred group of compounds of the invention are compounds of formula (Ia) in which:

represents

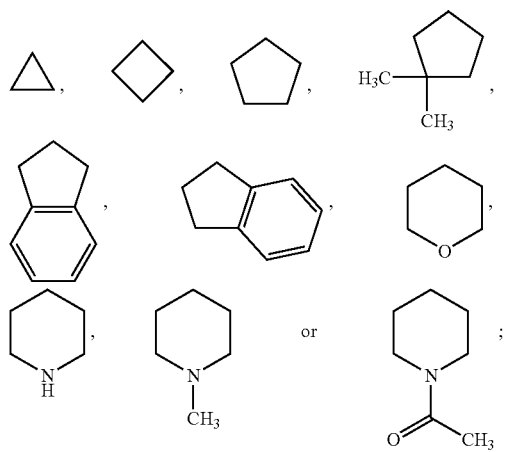

$R^9$ is hydrogen; $X^1$ represents $CR^{10}$ (especially where $R^{10}$ is $C_{1-4}$alkyl, e.g. methyl); $X^2$ represent $CR^{11}$ (especially where $R^{11}$ is $C_{1-4}$alkoxy, e.g. methoxy); $X^3$ represents CH; $R^5$ is a straight $C_{1-4}$alkylene chain (especially methylene); $R^2$ represents hydrogen; Y represents carboxy; $R^6$ of the group is attached at the ring 4 position; and the nitrogen atom of the group is attached at the ring 4'; and their prodrugs, and pharmaceutically acceptable salts and solvates (e.g. hydrates) of such compounds and their prodrugs.

Another particular group of compounds of the invention are compounds of formula (Ib):

(Ib)

in which $R^2$, $R^3$, $R^6$, $L^2$ and Y are as hereinbefore defined, X is O or $NR^{13}$ (in which $R^{13}$ is hydrogen or $C_{1-4}$ alkyl) and $R^{12}$ is hydrogen or an aryl group substituent and their prodrugs and pharmaceutically acceptable salts, and solvates (e.g. hydrates) of compounds of formula (Ib) and their prodrugs.

Compounds of formula (Ib) in which represents

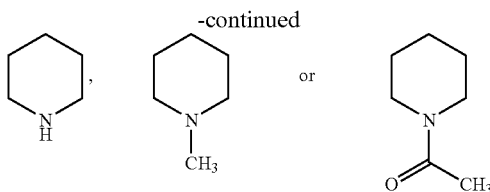

preferred.

Compounds of formula (Ib) in which $R^3$ represents optionally substituted aryl, especially optionally substituted phenyl, are preferred. Preferred optional substituents include $C_{1-4}$alkyl (e.g. methyl), $C_{1-4}$alkoxyl (e.g. methoxy), halo (e.g. fluoro) and $Y^1Y^2N-$ (e.g. dimethylamino). $R^3$ especially represents ortho-tolyl.

Compounds of formula (Ib) in which $R^{12}$ represents hydrogen, $C_{1-4}$alkyl (e.g. methyl or ethyl) or $C_{1-4}$alkoxyl (e.g. methoxy) are preferred.

Compounds of formula (Ib) in which $R^6$ represents a straight or branched $C_{1-6}$alkylene chain, especially a straight or branched $C_{1-4}$alkylene chain, more especially methylene, are preferred.

Compounds of formula (Ib) in which $R^2$ represents hydrogen are preferred.

Compounds of formula (Ib) in which $L^2$ represents methylene are preferred.

Compounds of formula (Ib) in which Y represents carboxy are preferred.

$R^6$ of the group

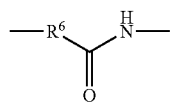

may preferably be attached at the ring 6 position.

The nitrogen atom of the group

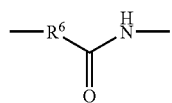

may preferably be attached at the ring 4' position.

A preferred group of compounds of the invention are compounds of formula (Ib) in which:

represents

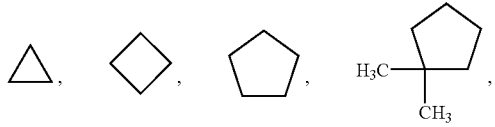

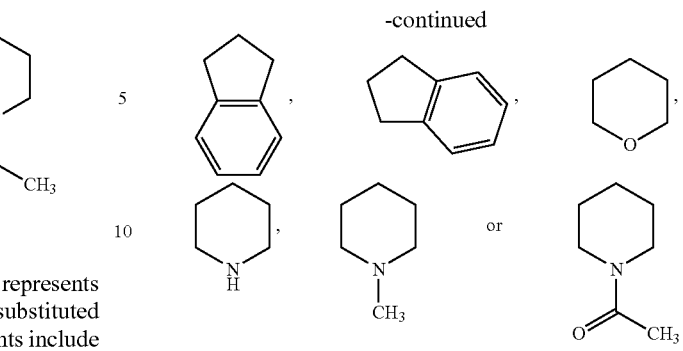

$R^3$ is optionally substituted phenyl (especially ortho-tolyl); X is O; $R^{12}$ represents hydrogen, $C_{1-4}$alkyl (e.g. methyl or ethyl) or $C_{1-4}$alkoxy (e.g. methoxy); $R^6$ is a straight or branched $C_{1-4}$alkylene chain, (especially methylene); $R^2$ is hydrogen; $L^2$ is methylene; Y is carboxy; $R^6$ of the group

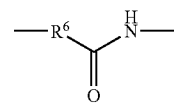

is attached at the ring 6 position; and the nitrogen atom of the group

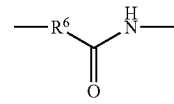

is attached at the ring 4' position; and the corresponding N-oxides, and their prodrugs; and pharmaceutically acceptable salts and solvates (e.g. hydrates) of such compounds and their N-oxides and prodrugs.

Particular compounds of the invention are selected from the compounds formed by joining the acyl carbon atom (C*) of one of the fragments (A1 to A36) shown in Table 1 to the nitrogen atom (N*) of one of the fragments (B1 to B4) shown in Table 2, and joining the carbon atom (C*) of the phenyl ring in one of the fragments (B1 to B4) shown in Table 2 to the carbon atom (C*) of one of the acidic fragments (C1 to C10) depicted in Table 3.

TABLE 1

| A1 | |
|---|---|
| A2 | |

TABLE 1-continued
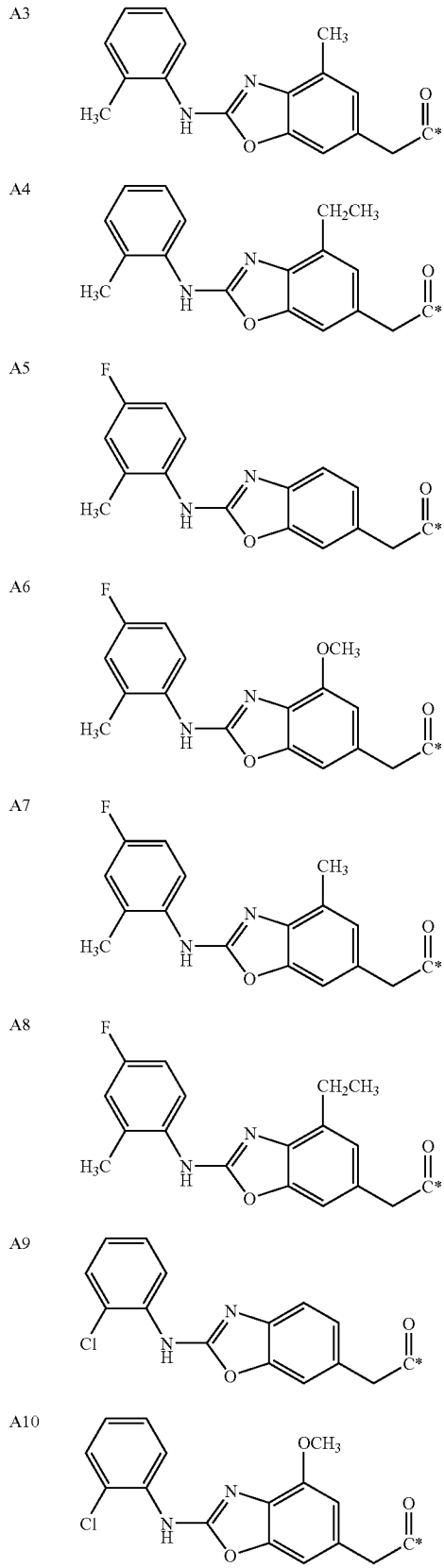
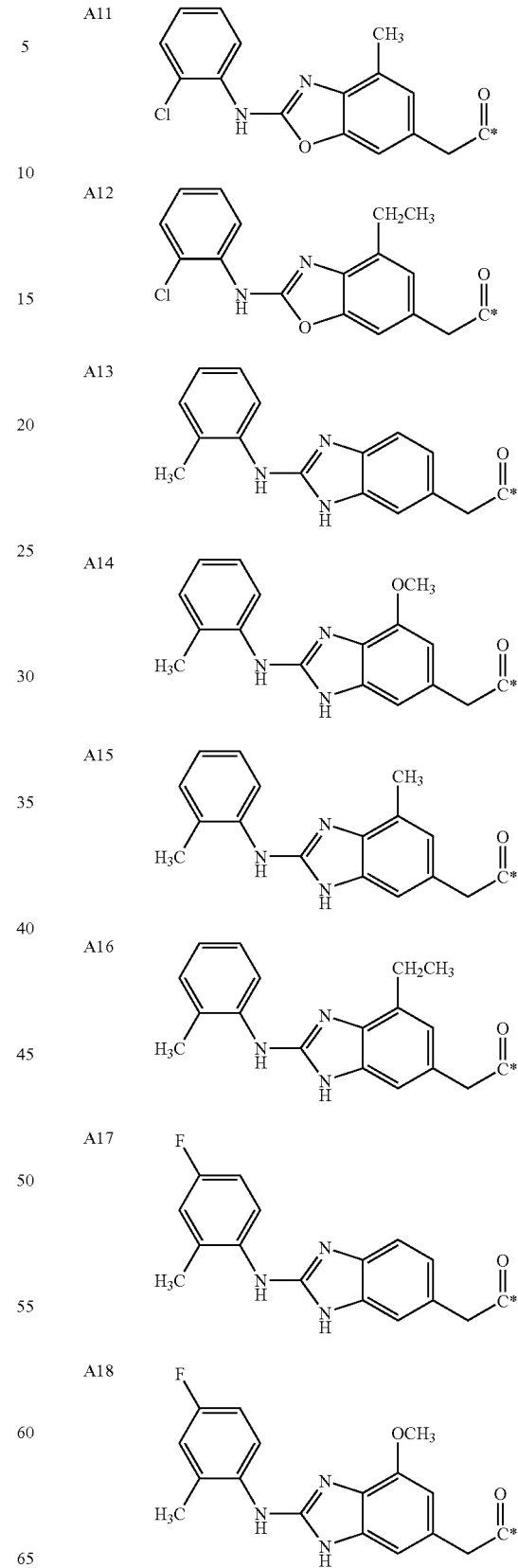

TABLE 1-continued
A19 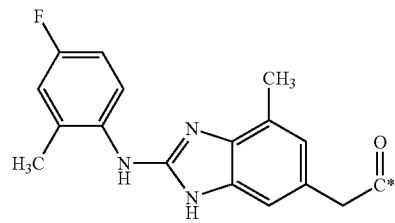
A20 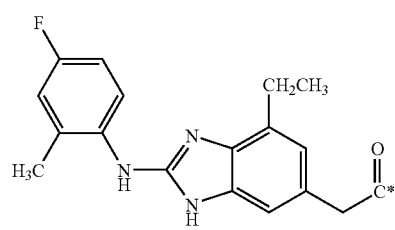
A21 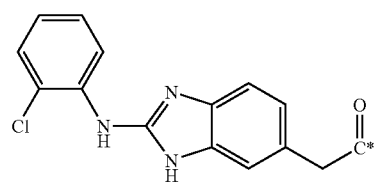
A22 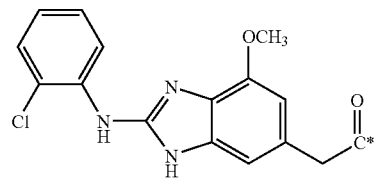
A23 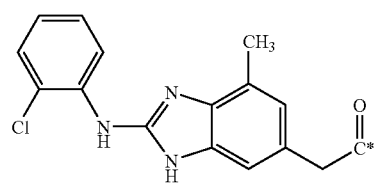
A24 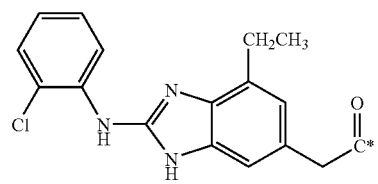
A25 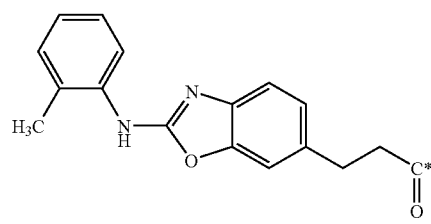
TABLE 1-continued
A26 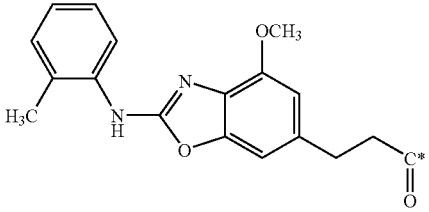
A27 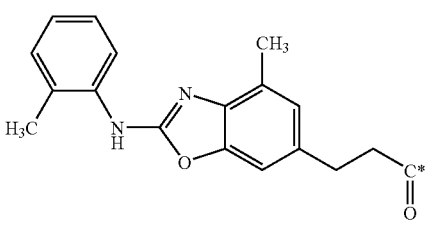
A28 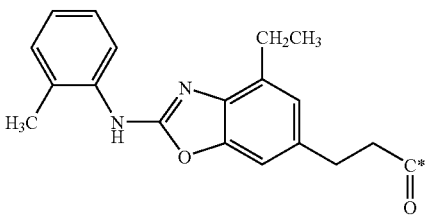
A29 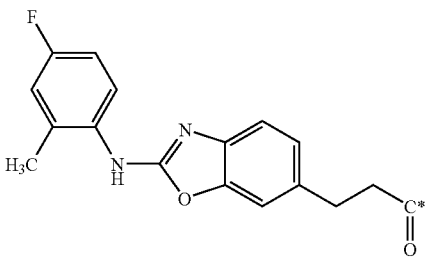
A30 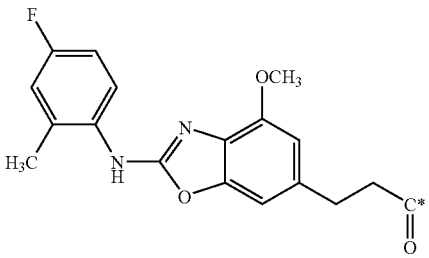
A31 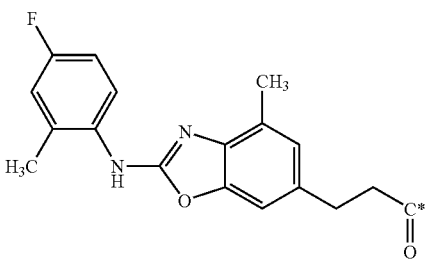

TABLE 1-continued

A32, A33, A34, A35, A36 (chemical structures)

TABLE 2

B1, B2, B3, B4 (chemical structures)

TABLE 3

C1, C2, C3, C4, C5, C6, C7 (chemical structures)

TABLE 3-continued

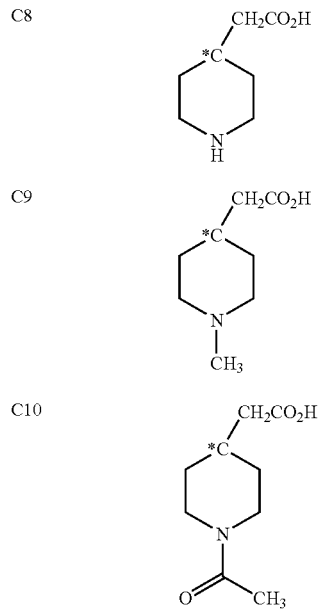

Further particular compounds of the invention are selected from the compounds formed by joining the acyl carbon atom (C*) of one of the fragments (A37 to A39) shown in Table 4 to the nitrogen atom (N*) of one of the fragments (B1 to B4) shown in Table 2, and joining the carbon atom (C*) of the phenyl ring in one of the fragments (B1 to B4) shown in Table 2 to the carbon atom (C*) of one of the acidic fragments (C1 to C10) depicted in Table 3.

TABLE 4

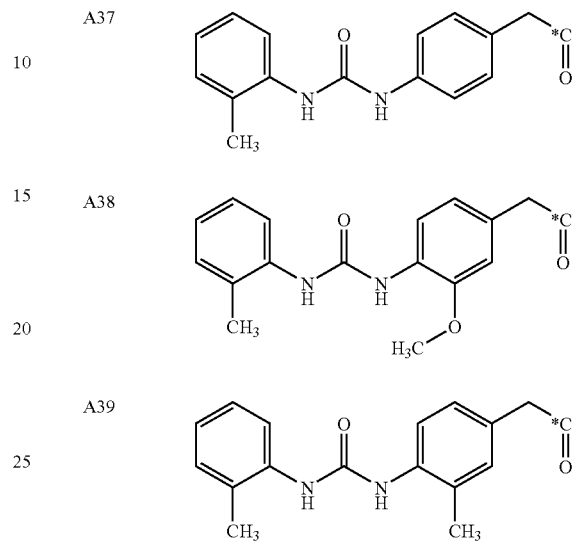

Particularly preferred examples of fragments "A", "B", and "C" are illustrated below:

| | | | | | |
|---|---|---|---|---|---|
| A1-B1-C1; | A1-B1-C2; | A1-B1-C3; | A1-B1-C4; | A1-B1-C5; | A1-B1-C6; |
| A1-B1-C7; | A1-B1-C8; | A1-B1-C9; | A1-B1-C10; | A2-B1-C1; | A2-B1-C2; |
| A2-B1-C3; | A2-B1-C4; | A2-B1-C5; | A2-B1-C6; | A2-B1-C7; | A2-B1-C8; |
| A2-B1-C9; | A2-B1-C10; | A3-B1-C1; | A3-B1-C2; | A3-B1-C3; | A3-B1-C4; |
| A3-B1-C5; | A3-B1-C6; | A3-B1-C7; | A3-B1-C8; | A3-B1-C9; | A3-B1-C10; |
| A4-B1-C1; | A4-B1-C2; | A4-B1-C3; | A4-B1-C4; | A4-B1-C5; | A4-B1-C6; |
| A4-B1-C7; | A4-B1-C8; | A4-B1-C9; | A4-B1-C10; | A5-B1-C1; | A5-B1-C2; |
| A5-B1-C3; | A5-B1-C4; | A5-B1-C5; | A5-B1-C6; | A5-B1-C7; | A5-B1-C8; |
| A5-B1-C9; | A5-B1-C10; | A6-B1-C1; | A6-B1-C2; | A6-B1-C3; | A6-B1-C4; |
| A6-B1-C5; | A6-B1-C6; | A6-B1-C7; | A6-B1-C8; | A6-B1-C9; | A6-B1-C10; |
| A7-B1-C1; | A7-B1-C2; | A7-B1-C3; | A7-B1-C4; | A7-B1-C5; | A7-B1-C6; |
| A7-B1-C7; | A7-B1-C8; | A7-B1-C9; | A7-B1-C10; | A8-B1-C1; | A8-B1-C2; |
| A8-B1-C3; | A8-B1-C4; | A8-B1-C5; | A8-B1-C6; | A8-B1-C7; | A8-B1-C8; |
| A8-B1-C9; | A8-B1-C10; | A9-B1-C1; | A9-B1-C2; | A9-B1-C3; | A9-B1-C4; |
| A9-B1-C5; | A9-B1-C6; | A9-B1-C7; | A9-B1-C8; | A9-B1-C9; | A9-B1-C10; |
| A10-B1-C1; | A10-B1-C2; | A10-B1-C3; | A10-B1-C4; | A10-B1-C5; | A10-B1-C6; |
| A10-B1-C7; | A10-B1-C8; | A10-B1-C9; | A10-B1-C10; | A11-B1-C1; | A11-B1-C2; |
| A11-B1-C3; | A11-B1-C4; | A11-B1-C5; | A11-B1-C6; | A11-B1-C7; | A11-B1-C8; |
| A11-B1-C9; | A11-B1-C10; | A12-B1-C1; | A12-B1-C2; | A12-B1-C3; | A12-B1-C4; |
| A12-B1-C5; | A12-B1-C6; | A12-B1-C7; | A12-B1-C8; | A12-B1-C9; | A12-B1-C10; |
| A13-B1-C1; | A13-B1-C2; | A13-B1-C3; | A13-B1-C4; | A13-B1-C5; | A13-B1-C6; |
| A13-B1-C7; | A13-B1-C8; | A13-B1-C9; | A13-B1-C10; | A14-B1-C1; | A14-B1-C2; |
| A14-B1-C3; | A14-B1-C4; | A14-B1-C5; | A14-B1-C6; | A14-B1-C7; | A14-B1-C8; |
| A14-B1-C9; | A14-B1-C10; | A15-B1-C1; | A15-B1-C2; | A15-B1-C3; | A15-B1-C4; |
| A15-B1-C5; | A15-B1-C6; | A15-B1-C7; | A15-B1-C8; | A15-B1-C9; | A15-B1-C10; |
| A16-B1-C1; | A16-B1-C2; | A16-B1-C3; | A16-B1-C4; | A16-B1-C5; | A16-B1-C6; |
| A16-B1-C7; | A16-B1-C8; | A16-B1-C9; | A16-B1-C10; | A17-B1-C1; | A17-B1-C2; |
| A17-B1-C3; | A17-B1-C4; | A17-B1-C5; | A17-B1-C6; | A17-B1-C7; | A17-B1-C8; |
| A17-B1-C9; | A17-B1-C10; | A18-B1-C1; | A18-B1-C2; | A18-B1-C3; | A18-B1-C4; |
| A18-B1-C5; | A18-B1-C6; | A18-B1-C7; | A18-B1-C8; | A18-B1-C9; | A18-B1-C10; |
| A19-B1-C1; | A19-B1-C2; | A19-B1-C3; | A19-B1-C4; | A19-B1-C5; | A19-B1-C6; |
| A19-B1-C7; | A19-B1-C8; | A19-B1-C9; | A19-B1-C10; | A20-B1-C1; | A20-B1-C2; |
| A20-B1-C3; | A20-B1-C4; | A20-B1-C5; | A20-B1-C6; | A20-B1-C7; | A20-B1-C8; |
| A20-B1-C9; | A20-B1-C10; | A21-B1-C1; | A21-B1-C2; | A21-B1-C3; | A21-B1-C4; |
| A21-B1-C5; | A21-B1-C6; | A21-B1-C7; | A21-B1-C8; | A21-B1-C9; | A21-B1-C10; |
| A22-B1-C1; | A22-B1-C2; | A22-B1-C3; | A22-B1-C4; | A22-B1-C5; | A22-B1-C6; |
| A22-B1-C7; | A22-B1-C8; | A22-B1-C9; | A22-B1-C10; | A23-B1-C1; | A23-B1-C2; |

-continued

| | | | | | |
|---|---|---|---|---|---|
| A23-B1-C3; | A23-B1-C4; | A23-B1-C5; | A23-B1-C6; | A23-B1-C7; | A23-B1-C8; |
| A23-B1-C9; | A23-B1-C10; | A24-B1-C1; | A24-B1-C2; | A24-B1-C3; | A24-B1-C4; |
| A24-B1-C5; | A24-B1-C6; | A24-B1-C7; | A24-B1-C8; | A24-B1-C9; | A24-B1-C10; |
| A25-B1-C1; | A25-B1-C2; | A25-B1-C3; | A25-B1-C4; | A25-B1-C5; | A25-B1-C6; |
| A25-B1-C7; | A25-B1-C8; | A25-B1-C9; | A25-B1-C10; | A26-B1-C1; | A26-B1-C2; |
| A26-B1-C3; | A26-B1-C4; | A26-B1-C5; | A26-B1-C6; | A26-B1-C7; | A26-B1-C8; |
| A26-B1-C9; | A26-B1-C10; | A27-B1-C1; | A27-B1-C2; | A27-B1-C3; | A27-B1-C4; |
| A27-B1-C5; | A27-B1-C6; | A27-B1-C7; | A27-B1-C8; | A27-B1-C9; | A27-B1-C10; |
| A28-B1-C1; | A28-B1-C2; | A28-B1-C3; | A28-B1-C4; | A28-B1-C5; | A28-B1-C6; |
| A28-B1-C7; | A28-B1-C8; | A28-B1-C9; | A28-B1-C10; | A29-B1-C1; | A29-B1-C2; |
| A29-B1-C3; | A29-B1-C4; | A29-B1-C5; | A29-B1-C6; | A29-B1-C7; | A29-B1-C8; |
| A29-B1-C9; | A29-B1-C10; | A30-B1-C1; | A30-B1-C2; | A30-B1-C3; | A30-B1-C4; |
| A30-B1-C5; | A30-B1-C6; | A30-B1-C7; | A30-B1-C8; | A30-B1-C9; | A30-B1-C10; |
| A31-B1-C1; | A31-B1-C2; | A31-B1-C3; | A31-B1-C4; | A31-B1-C5; | A31-B1-C6; |
| A31-B1-C7; | A31-B1-C8; | A31-B1-C9; | A31-B1-C10; | A32-B1-C1; | A32-B1-C2; |
| A32-B1-C3; | A32-B1-C4; | A32-B1-C5; | A32-B1-C6; | A32-B1-C7; | A32-B1-C8; |
| A32-B1-C9; | A32-B1-C10; | A33-B1-C1; | A33-B1-C2; | A33-B1-C3; | A33-B1-C4; |
| A33-B1-C5; | A33-B1-C6; | A33-B1-C7; | A33-B1-C8; | A33-B1-C9; | A33-B1-C10; |
| A34-B1-C1; | A34-B1-C2; | A34-B1-C3; | A34-B1-C4; | A34-B1-C5; | A34-B1-C6; |
| A34-B1-C7; | A34-B1-C8; | A34-B1-C9; | A34-B1-C10; | A35-B1-C1; | A35-B1-C2; |
| A35-B1-C3; | A35-B1-C4; | A35-B1-C5; | A35-B1-C6; | A35-B1-C7; | A35-B1-C8; |
| A35-B1-C9; | A35-B1-C10; | A36-B1-C1; | A36-B1-C2; | A36-B1-C3; | A36-B1-C4; |
| A36-B1-C5; | A36-B1-C6; | A36-B1-C7; | A36-B1-C8; | A36-B1-C9; | A36-B1-C10; |
| A37-B1-C1; | A37-B1-C2; | A37-B1-C3; | A37-B1-C4; | A37-B1-C5; | A37-B1-C6; |
| A37-B1-C7; | A37-B1-C8; | A37-B1-C9; | A37-B1-C10; | A38-B1-C1; | A38-B1-C2; |
| A38-B1-C3; | A38-B1-C4; | A38-B1-C5; | A38-B1-C6; | A38-B1-C7; | A38-B1-C8; |
| A38-B1-C9; | A38-B1-C10; | A39-B1-C1; | A39-B1-C2; | A39-B1-C3; | A39-B1-C4; |
| A39-B1-C5; | A39-B1-C6; | A39-B1-C7; | A39-B1-C8; | A39-B1-C9; | A39-B1-C10; |
| A1-B2-C1; | A1-B2-C2; | A1-B2-C3; | A1-B2-C4; | A1-B2-C5; | A1-B2-C6; |
| A1-B2-C7; | A1-B2-C8; | A1-B2-C9; | A1-B2-C10; | A2-B2-C1; | A2-B2-C2; |
| A2-B2-C3; | A2-B2-C4; | A2-B2-C5; | A2-B2-C6; | A2-B2-C7; | A2-B2-C8; |
| A2-B2-C9; | A2-B2-C10; | A3-B2-C1; | A3-B2-C2; | A3-B2-C3; | A3-B2-C4; |
| A3-B2-C5; | A3-B2-C6; | A3-B2-C7; | A3-B2-C8; | A3-B2-C9; | A3-B2-C10; |
| A4-B2-C1; | A4-B2-C2; | A4-B2-C3; | A4-B2-C4; | A4-B2-C5; | A4-B2-C6; |
| A4-B2-C7; | A4-B2-C8; | A4-B2-C9; | A4-B2-C10; | A5-B2-C1; | A5-B2-C2; |
| A5-B2-C3; | A5-B2-C4; | A5-B2-C5; | A5-B2-C6; | A5-B2-C7; | A5-B2-C8; |
| A5-B2-C9; | A5-B2-C10; | A6-B2-C1; | A6-B2-C2; | A6-B2-C3; | A6-B2-C4; |
| A6-B2-C5; | A6-B2-C6; | A6-B2-C7; | A6-B2-C8; | A6-B2-C9; | A6-B2-C10; |
| A7-B2-C1; | A7-B2-C2; | A7-B2-C3; | A7-B2-C4; | A7-B2-C5; | A7-B2-C6; |
| A7-B2-C7; | A7-B2-C8; | A7-B2-C9; | A7-B2-C10; | A8-B2-C1; | A8-B2-C2; |
| A8-B2-C3; | A8-B2-C4; | A8-B2-C5; | A8-B2-C6; | A8-B2-C7; | A8-B2-C8; |
| A8-B2-C9; | A8-B2-C10; | A9-B2-C1; | A9-B2-C2; | A9-B2-C3; | A9-B2-C4; |
| A9-B2-C5; | A9-B2-C6; | A9-B2-C7; | A9-B2-C8; | A9-B2-C9; | A9-B2-C10; |
| A10-B2-C1; | A10-B2-C2; | A10-B2-C3; | A10-B2-C4; | A10-B2-C5; | A10-B2-C6; |
| A10-B2-C7; | A10-B2-C8; | A10-B2-C9; | A10-B2-C10; | A11-B2-C1; | A11-B2-C2; |
| A11-B2-C3; | A11-B2-C4; | A11-B2-C5; | A11-B2-C6; | A11-B2-C7; | A11-B2-C8; |
| A11-B2-C9; | A11-B2-C10; | A12-B2-C1; | A12-B2-C2; | A12-B2-C3; | A12-B2-C4; |
| A12-B2-C5; | A12-B2-C6; | A12-B2-C7; | A12-B2-C8; | A12-B2-C9; | A12-B2-C10; |
| A13-B2-C1; | A13-B2-C2; | A13-B2-C3; | A13-B2-C4; | A13-B2-C5; | A13-B2-C6; |
| A13-B2-C7; | A13-B2-C8; | A13-B2-C9; | A13-B2-C10; | A14-B2-C1; | A14-B2-C2; |
| A14-B2-C3; | A14-B2-C4; | A14-B2-C5; | A14-B2-C6; | A14-B2-C7; | A14-B2-C8; |
| A14-B2-C9; | A14-B2-C10; | A15-B2-C1; | A15-B2-C2; | A15-B2-C3; | A15-B2-C4; |
| A15-B2-C5; | A15-B2-C6; | A15-B2-C7; | A15-B2-C8; | A15-B2-C9; | A15-B2-C10; |
| A16-B2-C1; | A16-B2-C2; | A16-B2-C3; | A16-B2-C4; | A16-B2-C5; | A16-B2-C6; |
| A16-B2-C7; | A16-B2-C8; | A16-B2-C9; | A16-B2-C10; | A17-B2-C1; | A17-B2-C2; |
| A17-B2-C3; | A17-B2-C4; | A17-B2-C5; | A17-B2-C6; | A17-B2-C7; | A17-B2-C8; |
| A17-B2-C9; | A17-B2-C10; | A18-B2-C1; | A18-B2-C2; | A18-B2-C3; | A18-B2-C4; |
| A18-B2-C5; | A18-B2-C6; | A18-B2-C7; | A18-B2-C8; | A18-B2-C9; | A18-B2-C10; |
| A19-B2-C1; | A19-B2-C2; | A19-B2-C3; | A19-B2-C4; | A19-B2-C5; | A19-B2-C6; |
| A19-B2-C7; | A19-B2-C8; | A19-B2-C9; | A19-B2-C10; | A20-B2-C1; | A20-B2-C2; |
| A20-B2-C3; | A20-B2-C4; | A20-B2-C5; | A20-B2-C6; | A20-B2-C7; | A20-B2-C8; |
| A20-B2-C9; | A20-B2-C10; | A21-B2-C1; | A21-B2-C2; | A21-B2-C3; | A21-B2-C4; |
| A21-B2-C5; | A21-B2-C6; | A21-B2-C7; | A21-B2-C8; | A21-B2-C9; | A21-B2-C10; |
| A22-B2-C1; | A22-B2-C2; | A22-B2-C3; | A22-B2-C4; | A22-B2-C5; | A22-B2-C6; |
| A22-B2-C7; | A22-B2-C8; | A22-B2-C9; | A22-B2-C10; | A23-B2-C1; | A23-B2-C2; |
| A23-B2-C3; | A23-B2-C4; | A23-B2-C5; | A23-B2-C6; | A23-B2-C7; | A23-B2-C8; |
| A23-B2-C9; | A23-B2-C10; | A24-B2-C1; | A24-B2-C2; | A24-B2-C3; | A24-B2-C4; |
| A24-B2-C5; | A24-B2-C6; | A24-B2-C7; | A24-B2-C8; | A24-B2-C9; | A24-B2-C10; |
| A25-B2-C1; | A25-B2-C2; | A25-B2-C3; | A25-B2-C4; | A25-B2-C5; | A25-B2-C6; |
| A25-B2-C7; | A25-B2-C8; | A25-B2-C9; | A25-B2-C10; | A26-B2-C1; | A26-B2-C2; |
| A26-B2-C3; | A26-B2-C4; | A26-B2-C5; | A26-B2-C6; | A26-B2-C7; | A26-B2-C8; |
| A26-B2-C9; | A26-B2-C10; | A27-B2-C1; | A27-B2-C2; | A27-B2-C3; | A27-B2-C4; |
| A27-B2-C5; | A27-B2-C6; | A27-B2-C7; | A27-B2-C8; | A27-B2-C9; | A27-B2-C10; |
| A28-B2-C1; | A28-B2-C2; | A28-B2-C3; | A28-B2-C4; | A28-B2-C5; | A28-B2-C6; |
| A28-B2-C7; | A28-B2-C8; | A28-B2-C9; | A28-B2-C10; | A29-B2-C1; | A29-B2-C2; |
| A29-B2-C3; | A29-B2-C4; | A29-B2-C5; | A29-B2-C6; | A29-B2-C7; | A29-B2-C8; |
| A29-B2-C9; | A29-B2-C10; | A30-B2-C1; | A30-B2-C2; | A30-B2-C3; | A30-B2-C4; |
| A30-B2-C5; | A30-B2-C6; | A30-B2-C7; | A30-B2-C8; | A30-B2-C9; | A30-B2-C10; |
| A31-B2-C1; | A31-B2-C2; | A31-B2-C3; | A31-B2-C4; | A31-B2-C5; | A31-B2-C6; |

-continued

| | | | | | |
|---|---|---|---|---|---|
| A31-B2-C7; | A31-B2-C8; | A31-B2-C9; | A31-B2-C10; | A32-B2-C1; | A32-B2-C2; |
| A32-B2-C3; | A32-B2-C4; | A32-B2-C5; | A32-B2-C6; | A32-B2-C7; | A32-B2-C8; |
| A32-B2-C9; | A32-B2-C10; | A33-B2-C1; | A33-B2-C2; | A33-B2-C3; | A33-B2-C4; |
| A33-B2-C5; | A33-B2-C6; | A33-B2-C7; | A33-B2-C8; | A33-B2-C9; | A33-B2-C10; |
| A34-B2-C1; | A34-B2-C2; | A34-B2-C3; | A34-B2-C4; | A34-B2-C5; | A34-B2-C6; |
| A34-B2-C7; | A34-B2-C8; | A34-B2-C9; | A34-B2-C10; | A35-B2-C1; | A35-B2-C2; |
| A35-B2-C3; | A35-B2-C4; | A35-B2-C5; | A35-B2-C6; | A35-B2-C7; | A35-B2-C8; |
| A35-B2-C9; | A35-B2-C10; | A36-B2-C1; | A36-B2-C2; | A36-B2-C3; | A36-B2-C4; |
| A36-B3-C5; | A36-B2-C6; | A36-B2-C7; | A36-B2-C8; | A36-B2-C9; | A36-B2-C10; |
| A37-B2-C1; | A37-B2-C2; | A37-B2-C3; | A37-B2-C4; | A37-B2-C5; | A37-B2-C6; |
| A37-B2-C7; | A37-B2-C8; | A37-B2-C9; | A37-B2-C10; | A38-B2-C1; | A38-B2-C2; |
| A38-B2-C3; | A38-B2-C4; | A38-B2-C5; | A38-B2-C6; | A38-B2-C7; | A38-B2-C8; |
| A38-B2-C9; | A38-B2-C10; | A39-B2-C1; | A39-B2-C2; | A39-B2-C3; | A39-B2-C4; |
| A39-B2-C5; | A39-B2-C6; | A39-B2-C7; | A39-B2-C8; | A39-B2-C9; | A39-B2-C10; |
| A1-B3-C1; | A1-B3-C2; | A1-B3-C3; | A1-B3-C4; | A1-B3-C5; | A1-B3-C6; |
| A1-B3-C7; | A1-B3-C8; | A1-B3-C9; | A1-B3-C10; | A2-B3-C1; | A2-B3-C2; |
| A2-B3-C3; | A2-B3-C4; | A2-B3-C5; | A2-B3-C6; | A2-B3-C7; | A2-B3-C8; |
| A2-B3-C9; | A2-B3-C10; | A3-B3-C1; | A3-B3-C2; | A3-B3-C3; | A3-B3-C4; |
| A3-B3-C5; | A3-B3-C6; | A3-B3-C7; | A3-B3-C8; | A3-B3-C9; | A3-B3-C10; |
| A4-B3-C1; | A4-B3-C2; | A4-B3-C3; | A4-B3-C4; | A4-B3-C5; | A4-B3-C6; |
| A4-B3-C7; | A4-B3-C8; | A4-B3-C9; | A4-B3-C10; | A5-B3-C1; | A5-B3-C2; |
| A5-B3-C3; | A5-B3-C4; | A5-B3-C5; | A5-B3-C6; | A5-B3-C7; | A5-B3-C8; |
| A5-B3-C9; | A5-B3-C10; | A6-B3-C1; | A6-B3-C2; | A6-B3-C3; | A6-B3-C4; |
| A6-B3-C5; | A6-B3-C6; | A6-B3-C7; | A6-B3-C8; | A6-B3-C9; | A6-B3-C10; |
| A7-B3-C1; | A7-B3-C2; | A7-B3-C3; | A7-B3-C4; | A7-B3-C5; | A7-B3-C6; |
| A7-B3-C7; | A7-B3-C8; | A7-B3-C9; | A7-B3-C10; | A8-B3-C1; | A5-B3-C2; |
| A8-B3-C3; | A8-B3-C4; | A8-B3-C5; | A8-B3-C6; | A8-B3-C7; | A8-B3-C8; |
| A8-B3-C9; | A8-B3-C10; | A9-B3-C1; | A9-B3-C2; | A9-B3-C3; | A9-B3-C4; |
| A9-B3-C5; | A9-B3-C6; | A9-B3-C7; | A9-B3-C8; | A9-B3-C9; | A9-B3-C10; |
| A10-B3-C1; | A10-B3-C2; | A10-B3-C3; | A10-B3-C4; | A10-B3-C5; | A10-B3-C6; |
| A10-B3-C7; | A10-B3-C8; | A10-B3-C9; | A10-B3-C10; | A11-B3-C1; | A11-B3-C2; |
| A11-B3-C3; | A11-B3-C4; | A11-B3-C5; | A11-B3-C6; | A11-B3-C7; | A11-B3-C8; |
| A11-B3-C9; | A11-B3-C10; | A12-B3-C1; | A12-B3-C2; | A12-B3-C3; | A12-B3-C4; |
| A12-B3-C5; | A12-B3-C6; | A12-B3-C7; | A12-B3-C8; | A12-B3-C9; | A12-B3-C10; |
| A13-B3-C1; | A13-B3-C2; | A13-B3-C3; | A13-B3-C4; | A13-B3-C5; | A13-B3-C6; |
| A13-B3-C7; | A13-B3-C8; | A13-B3-C9; | A13-B3-C10; | A14-B3-C1; | A14-B3-C2; |
| A14-B3-C3; | A14-B3-C4; | A14-B3-C5; | A14-B3-C6; | A14-B3-C7; | A14-B3-C8; |
| A14-B3-C9; | A14-B3-C10; | A15-B3-C1; | A15-B3-C2; | A15-B3-C3; | A15-B3-C4; |
| A15-B3-C5; | A15-B3-C6; | A15-B3-C7; | A15-B3-C8; | A15-B3-C9; | A15-B3-C10; |
| A16-B3-C1; | A16-B3-C2; | A16-B3-C3; | A16-B3-C4; | A16-B3-C5; | A16-B3-C6; |
| A16-B3-C7; | A16-B3-C8; | A16-B3-C9; | A16-B3-C10; | A17-B3-C1; | A17-B3-C2; |
| A17-B3-C3; | A17-B3-C4; | A17-B3-C5; | A17-B3-C6; | A17-B3-C7; | A17-B3-C8; |
| A17-B3-C9; | A17-B3-C10; | A18-B3-C1; | A18-B3-C2; | A15-B3-C3; | A18-B3-C4; |
| A18-B3-C5; | A18-B3-C6; | A18-B3-C7; | A18-B3-C8; | A18-B3-C9; | A18-B3-C10; |
| A19-B3-C1; | A19-B3-C2; | A19-B3-C3; | A19-B3-C4; | A19-B3-C5; | A19-B3-C6; |
| A19-B3-C7; | A19-B3-C8; | A19-B3-C9; | A19-B3-C10; | A20-B3-C1; | A20-B3-C2; |
| A20-B3-C3; | A20-B3-C4; | A20-B3-C5; | A20-B3-C6; | A20-B3-C7; | A20-B3-C8; |
| A20-B3-C9; | A20-B3-C10; | A21-B3-C1; | A21-B3-C2; | A21-B3-C3; | A21-B3-C4; |
| A21-B3-C5; | A21-B3-C6; | A21-B3-C7; | A21-B3-C8; | A21-B3-C9; | A21-B3-C10; |
| A22-B3-C1; | A22-B3-C2; | A22-B3-C3; | A22-B3-C4; | A22-B3-C5; | A22-B3-C6; |
| A22-B3-C7; | A22-B3-C8; | A22-B3-C9; | A22-B3-C10; | A23-B3-C1; | A23-B3-C2; |
| A23-B3-C3; | A23-B3-C4; | A23-B3-C5; | A23-B3-C6; | A23-B3-C7; | A23-B3-C8; |
| A23-B3-C9; | A23-B3-C10; | A24-B3-C1; | A24-B3-C2; | A24-B3-C3; | A24-B3-C4; |
| A24-B3-C5; | A24-B3-C6; | A24-B3-C7; | A24-B3-C8; | A24-B3-C9; | A24-B3-C10; |
| A25-B3-C1; | A25-B3-C2; | A25-B3-C3; | A25-B3-C4; | A25-B3-C5; | A25-B3-C6; |
| A25-B3-C7; | A25-B3-C8; | A25-B3-C9; | A25-B3-C10; | A26-B3-C1; | A26-B3-C2; |
| A26-B3-C3; | A26-B3-C4; | A26-B3-C5; | A26-B3-C6; | A26-B3-C7; | A26-B3-C8; |
| A26-B3-C9; | A26-B3-C10; | A27-B3-C1; | A27-B3-C2; | A27-B3-C3; | A27-B3-C4; |
| A27-B3-C5; | A27-B3-C6; | A27-B3-C7; | A27-B3-C8; | A27-B3-C9; | A27-B3-C10; |
| A28-B3-C1; | A28-B3-C2; | A28-B3-C3; | A28-B3-C4; | A28-B3-C5; | A28-B3-C6; |
| A28-B3-C7; | A28-B3-C8; | A28-B3-C9; | A28-B3-C10; | A29-B3-C1; | A29-B3-C2; |
| A29-B3-C3; | A29-B3-C4; | A29-B3-C5; | A29-B3-C6; | A29-B3-C7; | A29-B3-C8; |
| A29-B3-C9; | A29-B3-C10; | A30-B3-C1; | A30-B3-C2; | A30-B3-C3; | A30-B3-C4; |
| A30-B3-C5; | A30-B3-C6; | A30-B3-C7; | A30-B3-C8; | A30-B3-C9; | A30-B3-C10; |
| A31-B3-C1; | A31-B3-C2; | A31-B3-C3; | A31-B3-C4; | A31-B3-C5; | A31-B3-C6; |
| A31-B3-C7; | A31-B3-C8; | A31-B3-C9; | A31-B3-C10; | A32-B3-C1; | A32-B3-C2; |
| A32-B3-C3; | A32-B3-C4; | A32-B3-C5; | A32-B3-C6; | A32-B3-C7; | A32-B3-C8; |
| A32-B3-C9; | A32-B3-C10; | A33-B3-C1; | A33-B3-C2; | A33-B3-C3; | A33-B3-C4; |
| A33-B3-C5; | A33-B3-C6; | A33-B3-C7; | A33-B3-C8; | A33-B3-C9; | A33-B3-C10; |
| A34-B3-C1; | A34-B3-C2; | A34-B3-C3; | A34-B3-C4; | A34-B3-C5; | A34-B3-C6; |
| A34-B3-C7; | A34-B3-C8; | A34-B3-C9; | A34-B3-C10; | A35-B3-C1; | A35-B3-C2; |
| A35-B3-C3; | A35-B3-C4; | A35-B3-C5; | A35-B3-C6; | A35-B3-C7; | A35-B3-C8; |
| A35-B3-C9; | A35-B3-C10; | A36-B3-C1; | A36-B3-C2; | A36-B3-C3; | A36-B3-C4; |
| A36-B3-C5; | A36-B3-C6; | A36-B3-C7; | A36-B3-C8; | A36-B3-C9; | A36-B3-C10; |
| A37-B3-C1; | A37-B3-C2; | A37-B3-C3; | A37-B3-C4; | A37-B3-C5; | A37-B3-C6; |
| A37-B3-C7; | A37-B3-C8; | A37-B3-C9; | A37-B3-C10; | A38-B3-C1; | A38-B3-C2; |
| A38-B3-C3; | A38-B3-C4; | A38-B3-C5; | A38-B3-C6; | A38-B3-C7; | A38-B3-C8; |
| A38-B3-C9; | A38-B3-C10; | A39-B3-C1; | A39-B3-C2; | A39-B3-C3; | A39-B3-C4; |
| A39-B3-C5; | A39-B3-C6; | A39-B3-C7; | A39-B3-C8; | A39-B3-C9; | A39-B3-C10; |

-continued

| | | | | | |
|---|---|---|---|---|---|
| A1-B4-C1; | A1-B4-C2; | A1-B4-C3; | A1-B4-C4; | A1-B4-C5; | A1-B4-C6; |
| A1-B4-C7; | A1-B4-C8; | A1-B4-C9; | A1-B4-C10; | A2-B4-C1; | A2-B4-C2; |
| A2-B4-C3; | A2-B4-C4; | A2-B4-C5; | A2-B4-C6; | A2-B4-C7; | A2-B4-C8; |
| A2-B4-C9; | A2-B4-C10; | A3-B4-C1; | A3-B4-C2; | A3-B4-C3; | A3-B4-C4; |
| A3-B4-C5; | A3-B4-C6; | A3-B4-C7; | A3-B4-C8; | A3-B4-C9; | A3-B4-C10; |
| A4-B4-C1; | A4-B4-C2; | A4-B4-C3; | A4-B4-C4; | A4-B4-C5; | A4-B4-C6; |
| A4-B4-C7; | A4-B4-C8; | A4-B4-C9; | A4-B4-C10; | A5-B4-C1; | A5-B4-C2; |
| A5-B4-C3; | A5-B4-C4; | A5-B4-C5; | A5-B4-C6; | A5-B4-C7; | A5-B4-C8; |
| A5-B4-C9; | A5-B4-C10; | A6-B4-C1; | A6-B4-C2; | A6-B4-C3; | A6-B4-C4; |
| A6-B4-C5; | A6-B4-C6; | A6-B4-C7; | A6-B4-C8; | A6-B4-C9; | A6-B4-C10; |
| A7-B4-C1; | A7-B4-C2; | A7-B4-C3; | A7-B4-C4; | A7-B4-C5; | A7-B4-C6; |
| A7-B4-C7; | A7-B4-C8; | A7-B4-C9; | A7-B4-C10; | A8-B4-C1; | A8-B4-C2; |
| A8-B4-C3; | A8-B4-C4; | A8-B4-C5; | A8-B4-C6; | A5-B4-C7; | A8-B4-C8; |
| A8-B4-C9; | A8-B4-C10; | A9-B4-C1; | A9-B4-C2; | A9-B4-C3; | A9-B4-C4; |
| A9-B4-C5; | A9-B4-C6; | A9-B4-C7; | A9-B4-C8; | A9-B4-C9; | A9-B4-C10; |
| A10-B4-C1; | A10-B4-C2; | A10-B4-C3; | A10-B4-C4; | A10-B4-C5; | A10-B4-C6; |
| A10-B4-C7; | A10-B4-C8; | A10-B4-C9; | A10-B4-C10; | A11-B4-C1; | A11-B4-C2; |
| A11-B4-C3; | A11-B4-C4; | A11-B4-C5; | A11-B4-C6; | A11-B4-C7; | A11-B4-C8; |
| A11-B4-C9; | A11-B4-C10; | A12-B4-C1; | A12-B4-C2; | A12-B4-C3; | A12-B4-C4; |
| A12-B4-C5; | A12-B4-C6; | A12-B4-C7; | A12-B4-C8; | A12-B4-C9; | A12-B4-C10; |
| A13-B4-C1; | A13-B4-C2; | A13-B4-C3; | A13-B4-C4; | A13-B4-C5; | A13-B4-C6; |
| A13-B4-C7; | A13-B4-C8; | A13-B4-C9; | A13-B4-C10; | A14-B4-C1; | A14-B4-C2; |
| A14-B4-C3; | A14-B4-C4; | A14-B4-C5; | A14-B4-C6; | A14-B4-C7; | A14-B4-C8; |
| A14-B4-C9; | A14-B4-C10; | A15-B4-C1; | A15-B4-C2; | A15-B4-C3; | A15-B4-C4; |
| A15-B4-C5; | A15-B4-C6; | A15-B4-C7; | A15-B4-C8; | A15-B4-C9; | A15-B4-C10; |
| A16-B4-C1; | A16-B4-C2; | A16-B4-C3; | A16-B4-C4; | A16-B4-C5; | A16-B4-C6; |
| A16-B4-C7; | A16-B4-C8; | A16-B4-C9; | A16-B4-C10; | A17-B4-C1; | A17-B4-C2; |
| A17-B4-C3; | A17-B4-C4; | A17-B4-C5; | A17-B4-C6; | A17-B4-C7; | A17-B4-C8; |
| A17-B4-C9; | A17-B4-C10; | A18-B4-C1; | A18-B4-C2; | A18-B4-C3; | A18-B4-C4; |
| A18-B4-C5; | A18-B4-C6; | A18-B4-C7; | A18-B4-C8; | A18-B4-C9; | A18-B4-C10; |
| A19-B4-C1; | A19-B4-C2; | A19-B4-C3; | A19-B4-C4; | A19-B4-C5; | A19-B4-C6; |
| A19-B4-C7; | A19-B4-C8; | A19-B4-C9; | A19-B4-C10; | A20-B4-C1; | A20-B4-C2; |
| A20-B4-C3; | A20-B4-C4; | A20-B4-C5; | A20-B4-C6; | A20-B4-C7; | A20-B4-C8; |
| A20-B4-C9; | A20-B4-C10; | A21-B4-C1; | A21-B4-C2; | A21-B4-C3; | A21-B4-C4; |
| A21-B4-C5; | A21-B4-C6; | A21-B4-C7; | A21-B4-C8; | A21-B4-C9; | A21-B4-C10; |
| A22-B4-C1; | A22-B4-C2; | A22-B4-C3; | A22-B4-C4; | A22-B4-C5; | A22-B4-C6; |
| A22-B4-C7; | A22-B4-C8; | A22-B4-C9; | A22-B4-C10; | A23-B4-C1; | A23-B4-C2; |
| A23-B4-C3; | A23-B4-C4; | A23-B4-C5; | A23-B4-C6; | A23-B4-C7; | A23-B4-C8; |
| A23-B4-C9; | A23-B4-C10; | A24-B4-C1; | A24-B4-C2; | A24-B4-C3; | A24-B4-C4; |
| A24-B4-C5; | A24-B4-C6; | A24-B4-C7; | A24-B4-C8; | A24-B4-C9; | A24-B4-C10; |
| A25-B4-C1; | A25-B4-C2; | A25-B4-C3; | A25-B4-C4; | A25-B4-C5; | A25-B4-C6; |
| A25-B4-C7; | A25-B4-C8; | A25-B4-C9; | A25-B4-C10; | A26-B4-C1; | A26-B4-C2; |
| A26-B4-C3; | A26-B4-C4; | A26-B4-C5; | A26-B4-C6; | A26-B4-C7; | A26-B4-C8; |
| A26-B4-C9; | A26-B4-C10; | A27-B4-C1; | A27-B4-C2; | A27-B4-C3; | A27-B4-C4; |
| A27-B4-C5; | A27-B4-C6; | A27-B4-C7; | A27-B4-C8; | A27-B4-C9; | A27-B4-C10; |
| A28-B4-C1; | A28-B4-C2; | A28-B4-C3; | A28-B4-C4; | A28-B4-C5; | A28-B4-C6; |
| A28-B4-C7; | A28-B4-C8; | A28-B4-C9; | A28-B4-C10; | A29-B4-C1; | A29-B4-C2; |
| A29-B4-C3; | A29-B4-C4; | A29-B4-C5; | A29-B4-C6; | A29-B4-C7; | A29-B4-C8; |
| A29-B4-C9; | A29-B4-C10; | A30-B4-C1; | A30-B4-C2; | A30-B4-C3; | A30-B4-C4; |
| A30-B4-C5; | A30-B4-C6; | A30-B4-C7; | A30-B4-C8; | A30-B4-C9; | A30-B4-C10; |
| A31-B4-C1; | A31-B4-C2; | A31-B4-C3; | A31-B4-C4; | A31-B4-C5; | A31-B4-C6; |
| A31-B4-C7; | A31-B4-C8; | A31-B4-C9; | A31-B4-C10; | A32-B4-C1; | A32-B4-C2; |
| A32-B4-C3; | A32-B4-C4; | A32-B4-C5; | A32-B4-C6; | A32-B4-C7; | A32-B4-C8; |
| A32-B4-C9; | A32-B4-C10; | A33-B4-C1; | A33-B4-C2; | A33-B4-C3; | A33-B4-C4; |
| A33-B4-C5; | A33-B4-C6; | A33-B4-C7; | A33-B4-C8; | A33-B4-C9; | A33-B4-C10; |
| A34-B4-C1; | A34-B4-C2; | A34-B4-C3; | A34-B4-C4; | A34-B4-C5; | A34-B4-C6; |
| A34-B4-C7; | A34-B4-C8; | A34-B4-C9; | A34-B4-C10; | A35-B4-C1; | A35-B4-C2; |
| A35-B4-C3; | A35-B4-C4; | A35-B4-C5; | A35-B4-C6; | A35-B4-C7; | A35-B4-C8; |
| A35-B4-C9; | A35-B4-C10; | A36-B4-C1; | A36-B4-C2; | A3 6-B4-C3; | A36-B4-C4; |
| A36-B4-C5; | A36-B4-C6; | A36-B4-C7; | A36-B4-C8; | A36-B4-C9; | A36-B4-C10; |
| A37-B4-C1; | A37-B4-C2; | A37-B4-C3; | A37-B4-C4; | A37-B4-C5; | A37-B4-C6; |
| A37-B4-C7; | A37-B4-C8; | A37-B4-C9; | A37-B4-C10; | A38-B4-C1; | A38-B4-C2; |
| A38-B4-C3; | A38-B4-C4; | A38-B4-C5; | A38-B4-C6; | A38-B4-C7; | A38-B4-C8; |
| A38-B4-C9; | A38-B4-C10; | A39-B4-C1; | A39-B4-C2; | A39-B4-C3; | A39-B4-C4; |
| A39-B4-C5; | A39-B4-C6; | A39-B4-C7; | A39-B4-C8; | A39-B4-C9; | A39-B4-C10; |

Thus, for example, in the above list the compound denoted as A1-B1-C3 is the product of the combination of group A1 in Table 1 and B1 in Table 2 and C3 in Table 3, namely

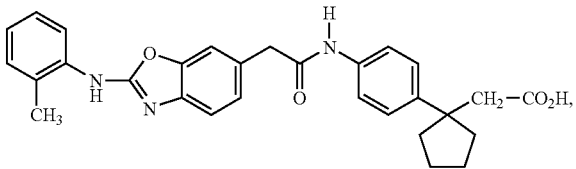

the compound denoted as A38-B1-C3 is the product of the combination of group A38 in Table 4 and B1 in Table 2 and C3 in Table 3, namely

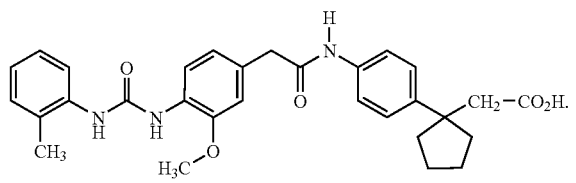

and the compound denoted as A3-B1-C7 is the product of the combination of group A3 in Table 1 and B1 in Table 2 and C7 in Table 3, namely

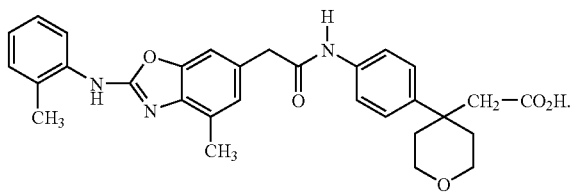

Preferred compounds of the invention are:
(1-{4-[2-(2-o-tolylamino-benzoxazol-6-yl)-acetylamino]-phenyl}-cyclopentyl)-acetic acid [compound denoted as A1-B1-C3];
[1-{4-[2-[3-methoxy-4-[3-o-tolyl-ureido]-phenyl]-acetylamino]-phenyl}-cyclopentyl]-acetic acid [compound denoted as A38-B1-C3];
(2-{4-[2-(2-o-tolylamino-benzoxazol-6-yl)-acetylamino]-phenyl}-indan-2-yl)-acetic acid [compound denoted as A1-B1-C5];
[2-(4-(2-(3-methoxy-4-(3-o-tolyl-ureido)-phenyl)-acetylamino)-phenyl)-indan-2-yl]-acetic acid [compound denoted as A38-B1-C5];
(4-(4-{2-[4-methyl-2-o-tolylamino-benzoxazol-6-yl]-acetylamino}-phenyl)-tetrahydro-pyran-4-yl)-acetic acid [compound denoted as A3-B1-C7];
(4-{4-[2-(2-o-tolylamino-benzoxazol-6-yl)-acetylamino]-phenyl}-tetrahydro-pyran-4-yl)-acetic acid [compound denoted as A1-B1-C7];
(1-{4-[2-(2-o-tolylamino-benzoxazol-6-yl)-acetylamino]-phenyl}-indan-1-yl)-acetic acid [compound denoted as A1-B1-C6];
(1-{4-[2-(2-o-tolylamino-benzoxazol-6-yl)-acetylamino]-phenyl}-cyclopropyl)-acetic acid [compound denoted as A1-B1-C1];
(1-{4-[2-(2-o-tolylamino-benzoxazol-6-yl)-acetylamino)-phenyl} -cyclobutyl)-acetic acid [compound denoted as A1-B1-C2];
[1-{4-[2-[4-methyl-2-o-tolylamino-benzoxazol-6-yl]-acetylamino]-phenyl}-cyclopentyl]-acetic acid [compound denoted as A3-B1-C3]; and
[1-{4-[{2-[3-methoxy-4-[3-o-tolyl-ureido]-phenyl]-acetyl}-methyl-amino]-phenyl }-cyclopentyl]-acetic acid [compound denoted as A38-B4-C3];

and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 (α4β1) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of α4β1 mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, autoimmune diabetes, autoimmune encephalomyelitis, collitis, atherosclerosis, peripheral vascular disease, cardiovascular disease, multiple sclerosis, stroke, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 (α4β1), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 (α4β1), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained.

Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I) wherein $R^1$, $R^2$, $L^1$, $L^2$ and

are as hereinbefore defined, and Y is carboxy may be prepared by hydrolysis of esters of formula (I) wherein $R^1$, $R^2$, $L^1$, $L^2$ and

are as hereinbefore defined and where the Y is a —$CO_2R^{14}$ group (in which $R^{14}$ is alkyl, alkenyl or arylalkyl). The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) wherein $R^1$, $R^2$, $L^1$, $L^2$ and

are as hereinbefore defined, and Y is carboxy may be prepared by acid catalysed removal of the tert-butyl group of tert-butyl esters of formula (I) wherein $R^1$, $R^2$, $L^1$, $L^2$ and

are as hereinbefore defined and Y is a —$CO_2R^{14}$ group (in which $R^{14}$ is tert-butyl), using standard reaction conditions, for example reaction with trifluoroacetic acid at a temperature at about room temperature.

As another example compounds of formula (I) wherein $R^1$, $R^2$, $L^1$, $L^2$ and

are as hereinbefore defined and Y is carboxy may be prepared by hydrogenation of compounds of formula (I) wherein $R^1$, $R^2$, $L^1$, $L^2$ and

are as hereinbefore defined and Y is a —$CO_2R^{14}$ group (in which $R^{14}$ is benzyl). The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

Esters of formula (I) wherein $R^1$, $R^2$, $L^2$ and

are as hereinbefore defined $L^1$ is an —$R^6$—$R^7$— linkage [in which $R^6$ is as hereinbefore defined and $R^7$ is —C(=O)—$NR^8$— (where $R^8$ is as hereinbefore defined)] and Y is a —$CO_2R^{14}$ group (in which $R^{14}$ is alkyl, alkenyl or arylalkyl) may be prepared by reaction of compounds of formula (II):

wherein $R^1$ and $R^6$ are as hereinbefore defined and $X^4$ is a hydroxy group or a halogen, preferably chlorine, atom, with amines of formula (III):

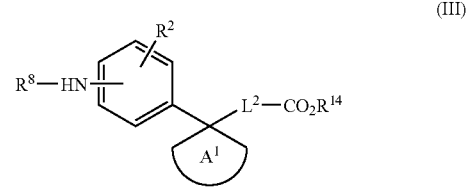

wherein $R^2$, $R^8$, $L^2$ and

are as hereinbefore defined and $R^{14}$ is alkyl, alkenyl or arylalkyl.

When $X^4$ is a hydroxy group the reaction may be carried out using standard peptide coupling procedures for example coupling in the presence of O-(7-azabenzotriazol-1-yl)-1,1,3,3-tetramethyluronium hexafluorophosphate and diisopropylethylamine in dimethylformamide (or tetrahydrofuran), at room temperature. When $X^4$ is a halogen atom the acylation reaction may be carried out with the aid of a base, such pyridine, preferably in a solvent such as tetrahydrofuran and at a temperature at about room temperature.

Esters of formula (I) wherein $R^1$, $R^2$, $L^2$ and

are as hereinbefore defined $L^1$ is an —$R^6$—$R^7$— linkage [in which $R^6$ is as hereinbefore defined, and $R^7$ is —$NR^8$—C(=O)— (where $R^8$ is as hereinbefore defined)] and Y is a —$CO_2R^{14}$ group (in which $R^{14}$ is alkyl, alkenyl or arylalkyl) may be prepared by reaction of compounds of formula (IV):

wherein $R^1$, $R^6$ and $R^8$ are as hereinbefore, with compounds of formula (V):

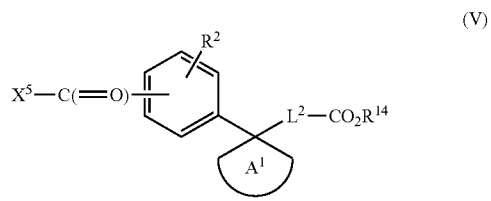

wherein $R^2$, $L^2$ and

are as hereinbefore defined, $R^{14}$ is alkyl, alkenyl or arylalkyl and $X^5$ is a hydroxy group or a halogen, preferably chlorine, atom, using procedures described hereinbefore for coupling acids or acid halides with amines.

Esters of formula (I) wherein $R^1$, $R^2$, $L^2$ and

are as hereinbefore defined, $L^1$ is a —$R^6$—$R^7$— linkage (in which $R^6$ is as hereinbefore defined and $R^7$ is —O—) and Y is a —$CO_2R^{14}$ group (in which $R^{14}$ is alkyl, alkenyl or arylalkyl) may be prepared by reaction of compounds of formula (VI):

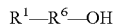 (VI)

wherein $R^1$ and $R^6$ are as hereinbefore defined with compounds of formula (VII):

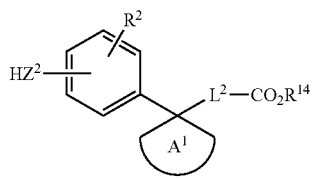 (VII)

wherein $R^2$, $L^2$ and

are as hereinbefore defined, $R^{14}$ is alkyl, alkenyl or arylalkyl and $Z^2$ is O, in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

Alternatively esters of formula (I) wherein $R^1$, $R^2$, $L^2$ and

are as hereinbefore defined, $L^1$ is a —$R^6$—$R^7$— linkage (in which $R^6$ is as hereinbefore defined and $R^7$ is —O—) and Y is a —$CO_2R^{14}$ group (in which $R^{14}$ is alkyl, alkenyl or arylalkyl) may be prepared by alkylation of compounds of formula (VII), wherein $R^2$, $L^2$ and

are as hereinbefore defined, $R^{14}$ is alkyl, alkenyl or arylalkyl and $Z^2$ is O with the appropriate alkyl bromides of formula (VIII):

 (VI)

wherein $R^1$ and $R^6$ are as hereinbefore defined and $X^6$ is a halogen, preferably bromo, atom using standard alkylation conditions. The alkylation may for example be carried out in the presence of a base, such as an alkali metal carbonate, e.g. potassium carbonate, or alkali metal hydride, e.g. sodium hydride, in dimethylformamide, or dimethyl sulfoxide, at a temperature from about 0° C. to about 100° C.

Esters of formula (I) wherein $R^1$, $R^2$, $L^2$ and

are as hereinbefore defined, $L^1$ is a —$R^6$—$R^7$— linkage (in which $R^6$ is as hereinbefore defined and $R^7$ is —S—) and Y is a —$CO_2R^{14}$ group (in which $R^{14}$ is alkyl, alkenyl or arylalkyl) may be similarly prepared by alkylation of compounds of formula (VII) wherein $R^2$, $L^2$ and

are as hereinbefore defined, $R^{14}$ is alkyl, alkenyl or arylalkyl and $Z^2$ is S.

Esters of formula (I) wherein $R^1$, $R^2$, $L^2$ and

are as hereinbefore defined, $L^1$ is a —$R^6$—$R^7$— linkage [in which $R^6$ is as hereinbefore defined and $R^7$ is —$NR^8$— (where $R^8$ is as hereinbefore defined)] and Y is a —$CO_2R^{14}$ group (in which $R^{14}$ is alkyl, alkenyl or arylalkyl) may be similarly prepared by alkylation of compounds of formula (III), wherein $R^2$, $R^8$, $L^2$ and

are as hereinbefore defined and $R^{14}$ is alkyl, alkenyl or arylalkyl.

Acids of formula (I) wherein $R^1$, $R^2$, $L^2$ and

are as hereinbefore defined, $L^1$ is a —$R^6$—$R^7$— linkage [in which $R^6$ is as hereinbefore defined and $R^7$ is —C(=O)—] and Y is carboxy may be prepared by reaction of esters of formula (IX):

$$R^1—R^6—CO_2R^{15} \qquad (IX)$$

wherein $R^1$ and $R^6$ are as hereinbefore defined and $R^{15}$ is lower alkyl, with Grignard reagents derived from reaction of compounds of formula (X):

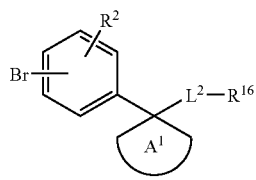

wherein $R^2$, $L^2$ and

are as hereinbefore defined and $R^{16}$ is a suitably protected carboxylic acid group, with magnesium using standard reaction conditions, followed by removal of the carboxylic acid protecting group.

Esters of formula (I) wherein $R^1$, $R^2$, $L^2$ and

are as hereinbefore defined, $L^1$ is a —$R^6$—$R^7$— linkage [in which $R^6$ is as hereinbefore defined and $R^7$ is —$NR^8$—C(=O)—NH— (where $R^8$ is as hereinbefore defined)] and Y is a —$CO_2R^{14}$ group (in which $R^{14}$ is alkyl, alkenyl or arylalkyl) may be prepared by reaction of compounds of formula (IV) wherein $R^1$, $R^6$ and $R^8$ are as hereinbefore defined, with isocyanates of formula (XI):

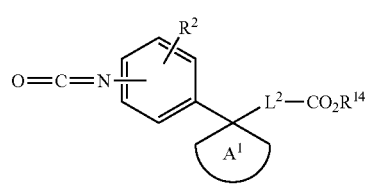

wherein $R^2$, $L^2$ and

are as hereinbefore defined and $R^{14}$ is alkyl, alkenyl or arylalkyl. The reaction is preferably carried out with the aid of a base, such as a tertiary amine, for example triethylamine, preferably in a solvent such as dichloromethane, and at a temperature at about room temperature.

Esters of formula (I) wherein $R^1$, $R^2$, $L^2$ and

are as hereinbefore defined, $L^1$ is a —$R^6$—$R^7$— linkage [in which $R^6$ is as hereinbefore defined and $R^7$ is —NH—C(=O)—$NR^8$— (where $R^8$ is as hereinbefore defined)] and Y, is a —$CO_2R^{14}$ group (in which $R^{14}$ is alkyl, alkenyl or arylalkyl) may be similarly prepared by reaction of amines of formula (III) wherein $R^2$, $R^8$, $L^2$ and

are as hereinbefore defined and $R^{14}$ is alkyl, alkenyl or arylalkyl with compounds of formula (XII):

$$R^1—R^6—N=C=O \qquad (XII)$$

wherein $R^1$ and $R^6$ are as hereinbefore defined.

Esters of formula (I) wherein $R^1$, $R^2$, $L^2$ and

are as hereinbefore defined, $L^1$ is a —$R^6$—$R^7$— linkage [in which $R^6$ is as hereinbefore defined and $R^7$ is —$SO_2$—$NR^8$— (where $R^8$ is as hereinbefore defined)] and Y is a —$CO_2R^{14}$ group (in which $R^{14}$ is alkyl, alkenyl or arylalkyl) may be prepared by reaction of compounds of formula (XIII):

$$R^1—R^6—SO_2Cl \qquad (XIII)$$

wherein $R^1$ and $R^6$ are as hereinbefore defined, with amines of formula (III) wherein $R^2$, $R^8$, $L^2$ and

are as hereinbefore defined and $R^{14}$ is alkyl, alkenyl or arylalkyl. The reaction is preferably carried out with the aid of a base, such as a tertiary amine, for example triethylamine, preferably in a solvent such as tetrahydrofuran and at a temperature at about room temperature.

Esters of formula (I) wherein $R^1$, $R^2$, $L^2$ and

are as hereinbefore defined, $L^1$ is a —$R^6$—$R^7$— linkage [in which $R^6$ is as hereinbefore defined and $R^7$ is —$NR^8$—$SO_2$— (where $R^8$ is as hereinbefore defined)] and Y is a —$CO_2R^{14}$ group (in which $R^{14}$ is alkyl, alkenyl or arylalkyl) may be similarly prepared by reaction of compounds of formula (IV) wherein $R^1$, $R^6$ and $R^8$ are as hereinbefore defined with sulfonyl chlorides of formula (XIV):

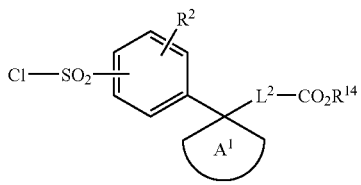

(XIV)

wherein $R^2$, $L^2$ and

are as hereinbefore defined and $R^{14}$ is alkyl, alkenyl or arylalkyl.

Esters of formula (I) wherein $R^1$, $R^2$, $L^2$ and

are as hereinbefore defined, $L^1$ is a —$R^6$—$R^7$— linkage [in which $R^6$ is as hereinbefore defined and $R^7$ is —O—C(=O)—] and Y is a —$CO_2R^{14}$ group (where $R^{14}$ is alkyl, alkenyl or arylalkyl) may be prepared by O-acylation of compounds of formula (VI) wherein $R^1$ and $R^6$ are as hereinbefore defined with compounds of formula (V) wherein $R^2$, $L^2$ and

are as hereinbefore defined, $R^{14}$ is alkyl, alkenyl or arylalkyl and $X^5$ is a chlorine atom.

The reaction may be carried using standard O-acylation conditions, for example reaction in the presence of a base, such as triethylamine or pyridine, at a temperature from about 0° C. to about room temperature.

Esters of formula (I) wherein $R^1$, $R^2$, $L^2$ and

are as hereinbefore defined, $L^1$ is a —$R^6$—$R^7$— linkage [in which $R^6$ is as hereinbefore defined and $R^7$ is —C(=O)—O—] and Y is a —$CO_2R^{14}$ group (where $R^{14}$ is alkyl, alkenyl or arylalkyl) may be similarly prepared by O-acylation of compounds of formula (VII) wherein $R^2$, $L^2$ and

are as hereinbefore defined, $R^{14}$ is alkyl, alkenyl or arylalkyl and $Z^2$ is O with compounds of formula (II) wherein $R^1$ and $R^6$ are as hereinbefore defined and $X^4$ is a chlorine atom.

Esters of formula (I) wherein $R^1$, $R^2$, $L^2$ and

are as hereinbefore defined, $L^1$ is a —$R^6$—$R^7$— linkage (in which $R^6$ is as hereinbefore defined and $R^7$ is —O—C(=O)—NH—) and Y is a —$CO_2R^{14}$ group (where $R^{14}$ is alkyl, alkenyl or arylalkyl) may be prepared by reaction of compounds of formula (VI) wherein $R^1$ and $R^6$ are as hereinbefore defined with isocyanates of formula (XI) wherein $R^2$, $L^2$ and

are as hereinbefore defined and $R^{14}$ is alkyl, alkenyl or arylalkyl. The reaction is preferably carried out with the aid of a base, such as a tertiary amine, for example triethylamine, preferably in a solvent such as dichloromethane, and at a temperature at about room temperature.

Esters of formula (I) wherein $R^1$, $R^2$, $L^2$ and

are as hereinbefore defined, $L^1$ is a —$R^6$—$R^7$— linkage (in which $R^6$ is as hereinbefore defined and $R^7$ is —NH—C(=O)—O—] and Y is a —$CO_2R^{14}$ group (where $R^{14}$ is alkyl, alkenyl or arylalkyl) may be similarly prepared by reaction of isocyanates of formula (XII) wherein $R^1$ and $R^6$ are as hereinbefore defined with compounds of formula (VII) wherein $R^2$, $L^2$ and

are as hereinbefore defined, $R^{14}$ is alkyl, alkenyl or arylalkyl and $Z^2$ is O.

Esters of formula (I) wherein $R^1$, $R^2$, $L^2$ and

are as hereinbefore defined, $L^1$ is a —$R^6$—$R^7$— linkage (in which $R^6$ is a straight or branched chain $C_{2-6}$alkenylene chain where the carbon-carbon double bond is directly attached to the phenyl ring and $R^7$ is a direct bond) and Y is a —$CO_2R^{14}$ group (where $R^{14}$ is alkyl, alkenyl or arylalkyl) may be prepared by reaction of compounds of formula (XV):

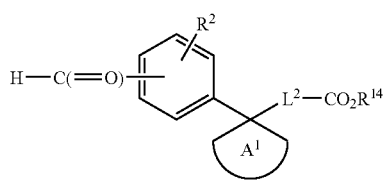
(XV)

wherein $R^2$, $L^2$ and

are as hereinbefore defined and $R^{14}$ is alkyl, alkenyl or arylalkyl, with an appropriate phosphorane (or phosphonate ester) of formula (XVI):

(XVI)

wherein $R^1$ is as hereinbefore defined, $R^{17}$ is a straight or branched chain $C_{1-5}$alkylene chain and $X^8$ is =$PPh_3^+Br^-$ (or —$P(=O)(OEt)_2$), using standard Wittig (or Horner-Wadsworth-Emmons) coupling procedures (for example those described in Tetrahedron Organic Chemistry Series Volume 11, Organic Synthesis Based On Name Reactions and Unnamed reactions, Editors, J. E. Baldwin and P. D. Magnus, pages 181 and 421).

According to a further feature of the present invention, compounds of the invention may be prepared by interconversion of other compounds of the invention.

For example compounds of formula (I) wherein $R^1$, $R^2$, $L^1$, $L^2$ and

are as hereinbefore defined and Y is —C(=O)—NHOH, may be prepared by reaction of compounds of formula (I) wherein $R^1$, $R^2$, $L^1$, $L^2$ and

are as hereinbefore defined and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl)hydroxylamine, O-(t-butyldimethylsilyl)-hydroxylamine, or O-(tetrahydropyranyl)hydroxylamine followed by treatment with acid.

As another example of the interconversion process, compounds of formula (I) wherein $R^1$, $R^2$, $L^2$,

and Y are as hereinbefore described and $L^1$ is a —$R^6$—$R^7$— linkage where $R^6$ is a straight or branched chain $C_{2-6}$alkylene chain and $R^7$ is a direct bond, may be similarly prepared by hydrogenation of the corresponding compounds of formula (I) in which $L^1$ is a —$R^6$—$R^7$— linkage where $R^6$ is a straight or branched chain $C_{2-6}$alkenylene chain and $R^7$ is a direct bond.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Acids of formula (II) wherein $R^1$ is $R^3Z^1$-Het- [in which $R^3$ is as hereinbefore defined, $Z^1$ is NH and Het is

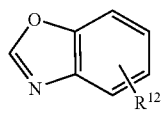

(where $R^{12}$ is as hereinbefore defined)], $R^6$ is as hereinbefore defined and $X^4$ is hydroxy may be prepared by reaction of compounds of formula (XVII):

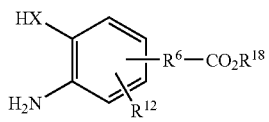

wherein $R^6$ and $R^{12}$ are as hereinbefore defined, $R^{18}$ is lower alkyl and X is O, with isocyanates of formula $R^3$—N=C=O in ethanol and at room temperature, followed by reaction with a carbodiimide, such as dicyclohexylcarbodiimide or diisopropylcarbodiimide in ethanol and at a temperature from about room temperature to about reflux temperature, and subsequent hydrolysis using standard conditions, for example those described hereinbefore.

Acids of formula (II) wherein $R^1$ is $R^3Z^1$-Het- [in which $R^3$ is as hereinbefore defined, $Z^1$ is NH and Het is

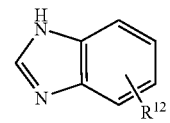

(where $R^{12}$ is as hereinbefore defined)], $R^6$ is as hereinbefore defined and $X^4$ is hydroxy may be similarly prepared from compounds of formula (XVII) wherein $R^6$, $R^{18}$ and $R^{12}$ are as hereinbefore defined and X is NH.

Compounds of general formula (XVII) wherein $R^{12}$ is as hereinbefore defined, $R^6$ is an alkylene chain, X is O, and $R^{18}$ is lower alkyl may be prepared by the reduction of compounds of general formula (XVIII):

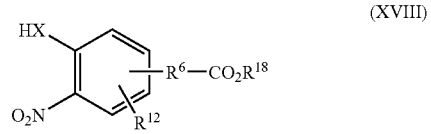

wherein $R^{12}$ and $R^6$ are as hereinbefore defined, X is O, and $R^{18}$ is lower alkyl. The reduction may be carried out using standard methods, such as those described hereinbefore, for example hydrogenation in the presence of palladium.

Compounds of general formula (XVIII) wherein $R^6$ and $R^{12}$ are as hereinbefore defined, X is O and $R^{18}$ is lower alkyl may be prepared by esterification of compounds of formula (XIX):

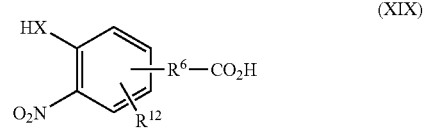

wherein $R^6$ and $R^{12}$ are as hereinbefore defined and X is O using standard methods as described hereinbefore, for example reaction with a lower alkyl alcohol (e.g. methanol) in the presence of a mineral acid, e.g. concentrated sulfuric acid.

Compounds of formula (XIX) wherein $R^6$ and $R^{12}$ are as hereinbefore defined and X is O may also be prepared by reaction of compounds of formula (XX):

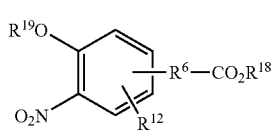

wherein $R^6$, $R^{12}$ and $R^{18}$ are as hereinbefore defined and $R^{19}$ is a suitable protecting group, such as alkylcarbonyl or arylcarbonyl, with a base, such as lithium hydroxide at a temperature at about room temperature.

Compounds of general formula (XIX) wherein $R^6$ and $R^{12}$ are as hereinbefore defined and X is O may also be prepared by reaction of compounds of general formula (XXI):

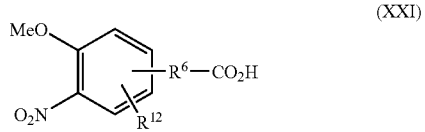

wherein $R^6$ and $R^{12}$ are as hereinbefore defined by reaction with pyridine hydrochloride at a temperature at about room temperature.

Compounds of formula (XX) wherein $R^6$, $R^{18}$ are as hereinbefore defined, $R^{12}$ is a lower alkyl group attached to the ring position adjacent to the nitro group and $R^{19}$ is a suitable protecting group, such as alkylcarbonyl or arylcarbonyl, may be prepared by reaction of compounds of formula (XXII):

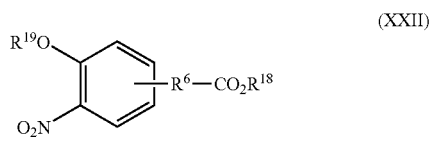

wherein $R^6$, $R^{18}$ are as hereinbefore defined and $R^{19}$ is a suitable protecting group, such as alkylcarbonyl or arylcarbonyl, with a lower alkyl magnesium halide, such as methyl magnesium chloride, in an inert solvent, such as tetrahydrofuran, and at a temperature at about –15° C.

Compounds of general formula (XXI) wherein $R^6$ and $R^{12}$ are as hereinbefore defined, may be prepared by the treatment of compounds of general formula (XXIII):

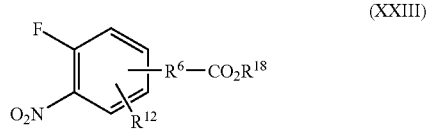

wherein $R^6$, $R^{12}$ and $R^{18}$ are as hereinbefore defined with sodium methoxide, followed by hydrolysis of the ester using standard conditions for example those described hereinbefore.

Compounds of general formula (XXI) wherein $R^6$ is as hereinbefore defined and $R^{12}$ is a methoxy group which is attached at the ring position adjacent to the nitro group, may be prepared by the treatment of compounds of general formula (XXIV):

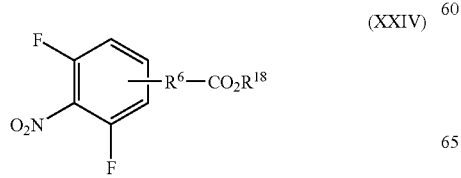

wherein $R^6$ and $R^{18}$ are as hereinbefore defined with sodium methoxide, followed by hydrolysis of the ester using standard conditions for example those described hereinbefore.

Acid chlorides of formula (II) wherein $R^1$ and $R^6$ are as hereinbefore defined and $X^4$ is a chlorine atom may be prepared from the corresponding acids of formula (II) wherein $R^1$ and $R^6$ are as hereinbefore defined and $X^4$ is hydroxy, by the application of standard procedures for the conversion of acids to acid chlorides for example by reaction with oxalyl chloride.

Compounds of formula (III) wherein $R^2$, $R^{14}$, $L^2$ and

are as hereinbefore defined and $R^8$ is hydrogen may be prepared by reduction of the corresponding nitro compounds of general formula (XXV):

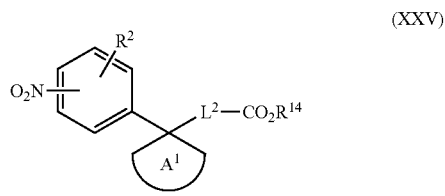

wherein $R^2$, $R^{14}$, $L^2$ and

are as hereinbefore defined. The reduction may be carried out using iron powder and ammonium chloride, in aqueous ethanol at a temperature at about reflux. The reduction may also be carried out by hydrogenation using standard conditions, for example those described hereinbefore.

Compounds of formula (XVII) wherein $R^6$, $R^{12}$ and $R^{18}$ are as hereinbefore defined and X is NH may be similarly prepared by reduction of the corresponding nitro-amino compounds or dinitro compounds.

Compounds of formula (III) wherein $R^2$, $R^{14}$, $L^2$ and

are as hereinbefore defined, and $R^8$ is hydrogen, i.e. compounds of formula (IIIa), may also be prepared as shown in scheme 1.

Scheme 1

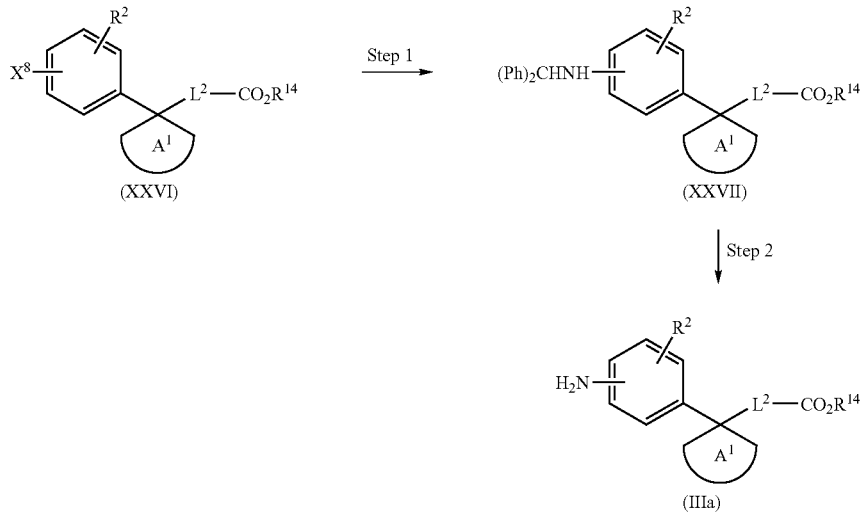

For example compounds of formula (XXVI), wherein $R^2$, $R^{14}$, $L^2$ and

are as hereinbefore defined and $X^8$ is a halogen, preferably chlorine, atom may be reacted, in step 1, with diphenylmethylamine in the presence of 2-(di-t-butylphosphino)biphenyl, palladium (II) acetate and sodium t-butoxide, in an inert solvent, such as toluene, and at a temperature at about 80° C. The resulting compounds of formula (XXVII) wherein $R^2$, $R^{14}$, $L^2$ and

are as hereinbefore defined may then be reacted, in Step 2, with trifluoroacetic acid in the presence of water and at a temperature from about room temperature to about 50° C. This procedure is particularly suitable for the preparation of compounds of formula (III) wherein $R^2$, $L^2$ and are as hereinbefore defined, $R^{14}$ is alkyl and $R^8$ is hydrogen and

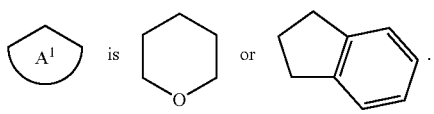

Esters of formula (XXVI) wherein $R^2$, $R^{14}$, $L^2$, $X^8$ and

are as hereinbefore defined may be prepared by esterification of acids of formula (XXVIII):

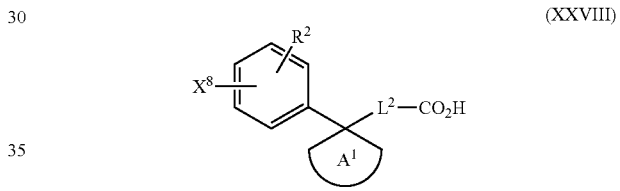

wherein $R^2$, $L^2$, $X^8$ and

are as hereinbefore defined, using standard esterification procedures, for example reaction with a lower alkyl alcohol (e.g. methanol) in the presence of an acid catalyst, such as hydrogen chloride or sulfuric acid.

Esters of formula (IX) wherein $R^1$ and $R^6$ are as hereinbefore defined and $R^{15}$ is lower alkyl may be similarly prepared from the corresponding acids of formula (II).

Acids of formula (XXVIII) wherein $R^2$ and

are as hereinbefore defined, $X^8$ is chloro and $L^2$ is methylene, i.e. compounds of formula (XXVIIIa), may be prepared as shown in scheme 2.

Scheme 2

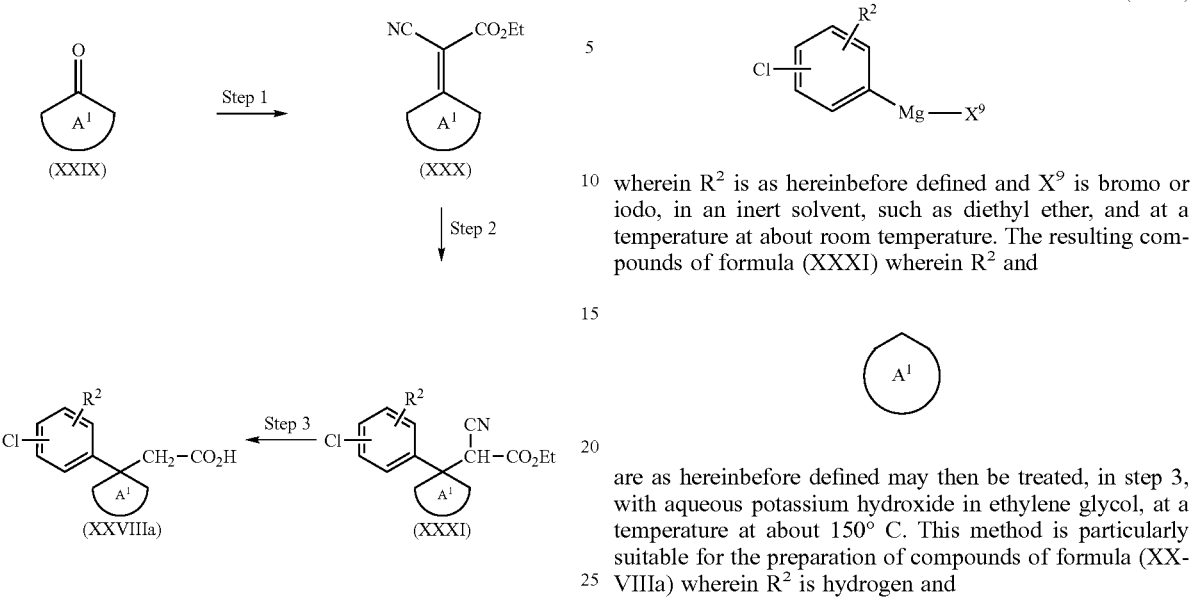

For example compounds of formula (XXIX) wherein

A¹ is as hereinbefore defined may be reacted, in step 1, with ethyl cyanoacetate in the presence of ammonium acetate, acetic acid and piperidine, in an inert solvent, such as toluene and at a temperature at about reflux temperature. The resulting compounds of formula (XXX) wherein

A¹ is as hereinbefore defined may then be reacted, in step 2, with a Grignard of formula (XXXII):

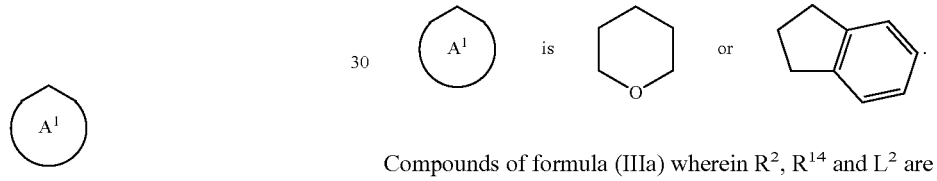

wherein $R^2$ is as hereinbefore defined and $X^9$ is bromo or iodo, in an inert solvent, such as diethyl ether, and at a temperature at about room temperature. The resulting compounds of formula (XXXI) wherein $R^2$ and

are as hereinbefore defined may then be treated, in step 3, with aqueous potassium hydroxide in ethylene glycol, at a temperature at about 150° C. This method is particularly suitable for the preparation of compounds of formula (XXVIIIa) wherein $R^2$ is hydrogen and

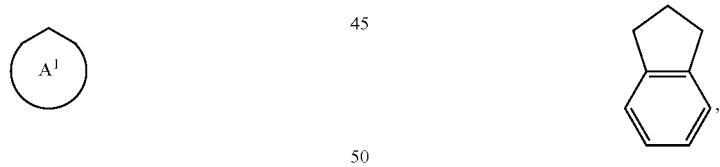

Compounds of formula (IIIa) wherein $R^2$, $R^{14}$ and $L^2$ are as hereinbefore defined and A¹ is

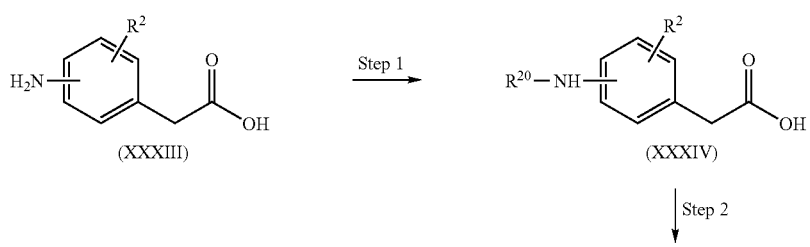

i.e. compounds of formula (IIIb), may be prepared as shown in scheme 3.

Scheme 3

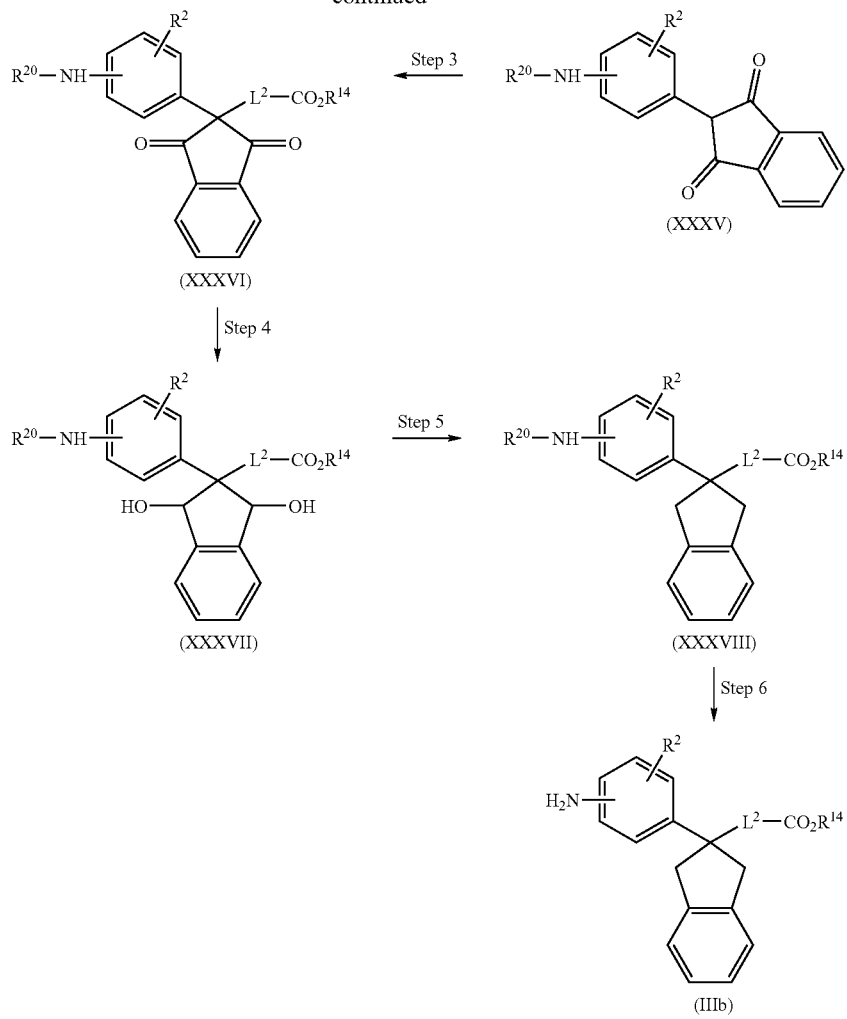

For example the amino group in aminophenyl-acetic acids of general formula (XXXIII), wherein $R^2$ is as hereinbefore defined, may be protected, in Step 1, with a suitable protecting group, such as acetyl, using standard reaction procedures. The resulting compounds of general formula (XXXIV), wherein $R^2$ and $R^{20}$ are as hereinbefore defined may then be reacted, in Step 2, with phthallic anhydride in the presence of triethylamine and acetic anhydride at a temperature at about 70° C. The resulting indan-1,3-dione of general formula (XXXV) wherein $R^2$ and $R^{20}$ are as hereinbefore may then be reacted, in Step 3, with an alkali metal alkoxide, such as sodium ethoxide followed by treated of the resulting anion with a chloroalkanoic acid ethyl ester of formula (XXXIX):

Cl-$L^2$-$CO_2R^{14}$      (XXXIX)

wherein $R^{14}$ and $L^2$ are as hereinbefore defined in the presence of sodium iodide and at a temperature at about 100° C. The resulting compounds of formula (XXXVI) wherein $R^2$, $R^{14}$, $R^{20}$ and $L^2$ are as hereinbefore defined may then be reduced, in Step 4, with sodium borohydride in absolute ethanol and at a temperature at about room temperature. The resulting compounds of formula (XXXVII) wherein $R^2$, $R^{14}$, $R^{20}$ and $L^2$ are as hereinbefore defined may then be further hydrogenated, in Step 5, in the presence of palladium black in acetic acid and at a temperature at about 50° C. The reduced compounds of formula (XXXVIII) wherein $R^2$, $R^{14}$, $R^{20}$ and $L^2$ are as hereinbefore defined may then be deprotected, in Step 6, using standard reaction conditions to furnish compounds of formula (XXXIX). This procedure is particularly suitable for the preparation of compounds of formula (IIIb) where $L^2$ is methylene.

Compounds of formula (IV) wherein $R^1$ and $R^6$ are as hereinbefore defined and $R^8$ is hydrogen may be prepared by reaction of compounds of formula (VIII) wherein $R^1$ and $R^6$ are as hereinbefore defined and $X^6$ is bromo with phthalimide potassium salt in dimethylformamide followed by reaction with hydrazine hydrate in ethanol (for example using the conditions described by O. Diouf et al., Heterocycles, 1995, 41, page 1219–1233).

Compounds of formula (IV) wherein $R^1$ and $R^6$ are as hereinbefore defined and $R^8$ is methyl may be prepared by treatment of the corresponding compounds of formula (IV) wherein $R^1$ and $R^6$ are as hereinbefore and $R^8$ is hydrogen with formic acetic anhydride followed by reduction with lithium aluminium hydride according to the procedure described by L. G. Humber et al, J. Med. Chem., 1971, 14, page 982.

Compounds of formula (VI) wherein $R^1$ is as hereinbefore and $R^6$ is methylene, may be prepared by reduction of esters of formula (XXXX):

$$R^1—CO_2R^{21} \quad (XXXX)$$

wherein $R^1$ is as hereinbefore defined and $R^{21}$ is alkyl. The reduction may conveniently be carried out with diisobutylaluminium hydride in an inert solvent, such as tetrahydrofuran, at a temperature from about −78° C. to about room temperature. The reduction may also be carried out with lithium aluminium hydride in an inert solvent, such as an ether, for example diethyl ether, at a temperature from about room temperature to about reflux.

Compounds of formula (VIII) wherein $R^1$, $R^6$ is an alkylene chain and $X^6$ is bromo may be prepared by reaction of compounds of formula (VI), wherein $R^1$ is as hereinbefore defined and $R^6$ is an alkylene chain, with phosphorus tribromide in an inert solvent, such as carbon tetrachloride, and at a temperature at about room temperature.

Compounds of formula (XII) wherein $R^1$ and $R^6$ are as hereinbefore defined may be prepared from compounds of formula (IV) wherein $R^1$ and $R^6$ are as hereinbefore defined and $R^8$ is hydrogen with phosgene following standard reaction conditions for the conversion of amines to isocyanates.

Compounds of formula (XIII) wherein $R^1$ and $R^6$ are as hereinbefore defined may be prepared by reaction of compounds of formula (VIII) wherein $R^1$ and $R^6$ are as hereinbefore defined and $X^6$ is a bromine atom with sodium sulfite then with phosphorus trichloride according to the procedure described by P. N. Culshaw and J. C. Walton, J. Chem. Soc., Perkin Trans II, 1991, 8, page 1201–1208.

Compounds of formula (XVI) wherein $R^1$ is as hereinbefore defined, $R^{17}$ is a straight or branched chain $C_{1-5}$alkylene chain and $X^8$ is $=PPh_3^+Br^-$ may be prepared by reaction of compounds of formula (VIII) wherein $R^1$ is as hereinbefore defined, $R^6$ is a straight or branched chain $C_{1-5}$alkylene chain and $X^6$ is a bromine atom by reaction with triphenylphosphine in an inert solvent and at a temperature from about room temperature to about reflux temperature of the solvent.

Compounds of formula (XXV) wherein $R^2$ and

are as hereinbefore defined, $R^{14}$ is alkyl and $L^2$ is methylene, may be prepared by treatment of compounds of formula (XXXXI):

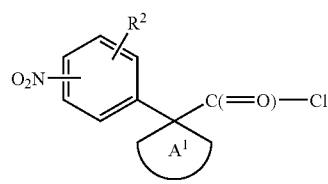

(XXXXI)

wherein $R^2$ and

are as hereinbefore defined with (i) trimethylsilyldiazomethane in an inert solvent, such as acetonitrile, and at a temperature at about 0° C. then with (ii) silver benzoate and an alkyl alcohol of formula $R^{14}$—OH in the presence of triethylamine and at reflux temperature. This procedure is particularly suitable for the preparation of compounds of formula (XXXXI) wherein

is and $R^{14}$ is tert-butyl.

The present invention is further exemplified but not limited by the following illustrative Examples and Reference Examples.

High Pressure Liquid Chromatography/Mass Spectrometry (LC-MS) conditions for determination of retention times ($R_T$) were as follows: 3 micron Luna C18 (2) HPLC column (30 mm×4.6mm) operated under gradient elution conditions with mixtures of (A) water containing 0.1% formic acid and (B) acetonitrile containing 0.1% formic acid as the mobile phase gradient: 0.00 minutes, 95% A:5% B; 0.50 minutes, 95% A:5% B; 4.50 minutes, 5% A:95% B; 5.00 minutes, 5% A:95% B; 5.50 minutes, 95% A:5% B; flow rate 2 µl/minute with approximately 2001/minute split to the Mass Spectrometer; injection volume 10–40 µl; in line Diode Array (220–450 nm), in line Evaporative light scattering (ELS) detection ELS-temperature 50° C., Gain 8–1.8 ml/minute; Source temperature 150° C.

Compounds have been named using Autonom Standard, Version 2.2.

EXAMPLE 1

(1-{4-[2-(2-o-Tolylamino-benzoxazol-6-yl)-acetylamino]-phenyl}-cyclopentyl)-acetic acid

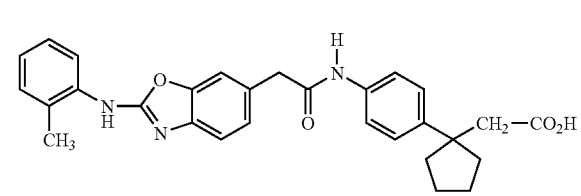

A solution of [1-{4-[2-[2-o-tolylamino-benzoxazol-6-yl]-acetylamino]-phenyl}-cyclopentyl]-acetic acid tert-butyl ester [0.36 g, Reference Example 1(a)] in a mixture of trifluoroacetic acid (12 mL), dichloromethane (2.25 mL) and water (1.5 mL) was stirred at room temperature for 1.5 hours. The resulting turquoise solution was evaporated and the residue was chased with toluene to yield an amber gum which was recrystallised from a mixture of acetonitrile and water to give the title compound (0.25 g) as an off white solid, m.p. 123–126° C. LC-MS: $R_T$=3.51 minutes, MS(ES$^+$): 506.6(M+Na)$^+$, 484.6(M+H)$^+$; MS(ES$^-$): 482.4 (M–H)$^-$.

EXAMPLE 2

[1-{4-[2-[3-Methoxy-4-[3-o-tolyl-ureido]-phenyl]-acetylamino]-phenyl}-cyclopentyl]-acetic acid

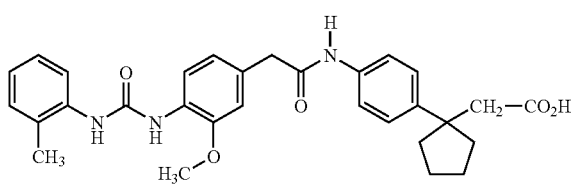

A solution of [1-{4-[2-[3-methoxy-4-[3-o-tolyl-ureido]-phenyl]-acetylamino]-phenyl}-cyclopentyl]-acetic acid tert-butyl ester (0.29 g, Reference Example 8) in a mixture of trifluoroacetic acid (7.5 mL), dichloromethane (1.5 mL) and water (1 mL) was stirred at room temperature for 1.5 hours and then evaporated. The residue was chased with toluene to yield a green glass, which was subjected to preparative HPLC [HyperPrep HS C-18 silica column using methanol with 0.05% trifluoroacetic acid and water with 0.05% trifluoroacetic acid as the mobile phase] to give the title compound (0.05 g) as a white solid, m.p. 223–226° C. LC-MS: $R_T$=3.51 minutes, MS(ES$^+$): 538(M+Na$^+$), 516(M+H)$^+$, 554(M+K)$^+$; MS(ES$^-$): 514(M–H)$^-$.

EXAMPLE 3

(2-{4-[2-(2-o-Tolylamino-benzoxazol-6-yl)-acetylamino]-phenyl}-indan-2-yl)-acetic acid

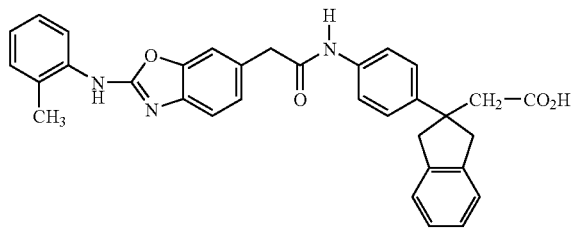

A solution of (2-(4-(2-(2-o-tolylamino-benzoxazol-6-yl)-acetylamino)-phenyl)-indan-2-yl)-acetic acid ethyl ester [0.297 g, Reference Example 9(a)] in ethanol (10 mL) was treated with aqueous sodium hydroxide (1.61 mL, 1N) and the mixture was heated at reflux temperature for 6 hours and then left at room temperature overnight and then evaporated. The residue was treated with water (30 mL) and the resulting mixture was acidified to pH 1 by addition of hydrochloric acid (1N) then extracted with ethyl acetate. The ethyl acetate extract was dried over magnesium sulfate and then evaporated. The residue was dissolved in hot acetonitrile and the solution was treated with charcoal then filtered. The filtrate was evaporated to give the title compound (0.07 g) as a biscuit coloured solid.

EXAMPLE 4

[2-(4-(2-(3-Methoxy-4-(3-o-tolyl-ureido)-phenyl)-acetylamino)-phenyl)-indan-2-yl]-acetic acid

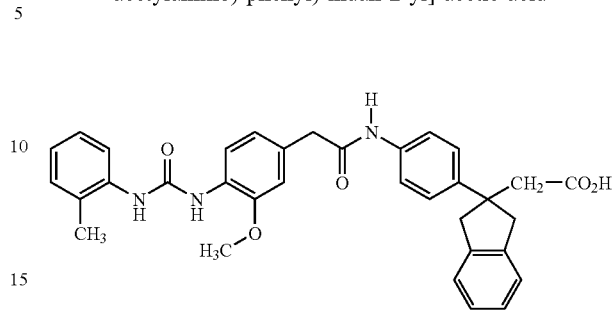

A solution of [2-(4-(2-(3-methoxy-4-(3-o-tolyl-ureido)-phenyl)-acetylamino)-phenyl)-indan-2-yl]-acetic acid ethyl ester (0.06 g, Reference Example 16) in ethanol (10 mL) was treated with aqueous sodium hydroxide (300 μL, 1N) and the mixture was heated at reflux temperature for 8 hours and then left at room temperature overnight and then evaporated. The residue was treated with water (20 mL) and the mixture was warmed to aid dissolution. This solution was acidified to pH 1 by addition of hydrochloric acid (1N) when a precipitate was formed. The mixture was kept at 0° C. for 30 minutes then extracted with ethyl acetate. The ethyl acetate extract was dried over magnesium sulfate and then evaporated. The residual white solid was subjected to chromatography [gradient HPLC using 50% acetonitrile and water, 1 mL/minute] to give the title compound (0.03 g) as a white solid.

EXAMPLE 5

(4-(4-{2-[4-Methyl-2-o-tolylamino-benzoxazol-6-yl]-acetylamino}-phenyl)-tetrahydro-pyran-4-yl)-acetic acid

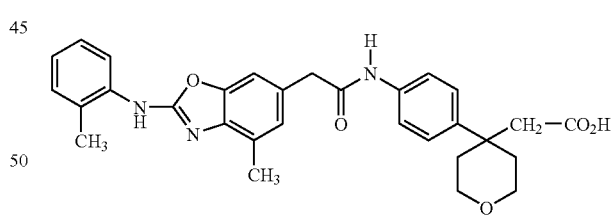

A solution of (4-(4-{2-[4-methyl-2-o-tolylamino-benzoxazol-6-yl]-acetylamino}-phenyl)-tetrahydro-pyran-4-yl)-acetic acid methyl ester [0.178 g, Reference Example 17(a)] in degassed ethanol (30 mL) was treated with sodium hydroxide solution (1 mL, 1N) and the mixture was stirred under nitrogen and at reflux temperature for 6 hours. The resulting red solution was evaporated and the residue was subjected to preparative HPLC on a Hypersil Elite C18 column eluting initially with a mixture of acetonitrile, water and trifluoroacetic acid (25:75:0.1, v/v/v) and then 1% acetonitrile/minute gradient to give the title compound (0.052 g) as a solid. LC-MS: $R_T$=3.30 minutes, MS(ES$^+$): 514.06(M+H)$^+$; MS(ES$^-$): 512.08(M–H)$^-$.

EXAMPLE 6

(4-{4-[2-(2-o-Tolylamino-benzoxazol-6-yl)-acetylamino]-phenyl}-tetrahydro-pyran-4-yl)-acetic acid

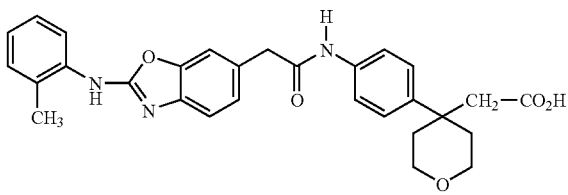

A solution of (4-(4-{2-[2-o-tolylamino-benzoxazol-6-yl]-acetylamino}-phenyl)-tetrahydro-pyran-4-yl)-acetic acid methyl ester [0.2 g, Reference Example 17(b)] in ethanol (25 mL) was treated with sodium hydroxide solution (2 mL, 1N) and the mixture was stirred under argon and at reflux temperature for 3 hours. The reaction mixture was evaporated and the residue was dissolved in water (25 mL). This solution was washed with diethyl ether (10 mL) and then acidified to pH 1 by addition of hydrochloric acid (3 mL, 1N). The resulting precipitate was filtered, then washed four times with water (5 mL) and then dried at 60° C. under high vacuum to give the title compound (0.1 g) as an off-white solid. LC-MS: $R_T$=3.10 minutes, MS(ES$^+$): 500(M+H)$^+$.

EXAMPLE 7

(1-{4-[2-(2-o-Tolylamino-benzoxazol-6-yl)-acetylamino]-phenyl}-indan-1-yl)-acetic acid

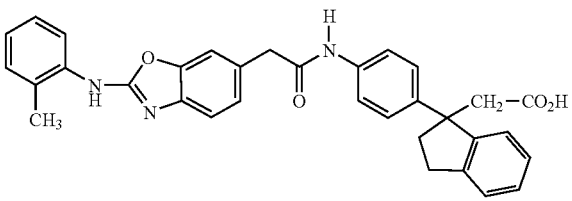

A solution of (1-{4-[2-(2-o-tolylamino-benzoxazol-6-yl)-acetylamino]-phenyl}-indan-1-yl)-acetic acid methyl ester [0.028 g, Reference Example 9(b)] in ethanol (5 mL) was treated with aqueous sodium hydroxide (0.3 mL, 1N) and the mixture was heated at reflux temperature for 2.5 hours. The mixture was then treated with a further aliquot of aqueous sodium hydroxide (0.15 mL, 1N) and heating at reflux temperature for continued for a further hour. The reaction mixture was concentrated to about 2 mL and then treated with water (12 mL). The resulting solution was acidified to pH 1 by addition of hydrochloric acid (1.75 mL, 1N) with stirring when a solid was deposited. The mixture was ice-cooled and then filtered. The solid was washed three times with water (3 mL) and then dried at 60° C. under vacuum to give the title compound (0.017 g) as a fawn coloured solid. LC-MS: $R_T$=3.69 minutes, MS(ES$^+$): 532 (M+H)$^+$.

EXAMPLE 8

(1-{4-[2-[2-o-Tolylamino-benzoxazol-6-yl]-acetylamino]-phenyl}-cyclopropyl)-acetic acid

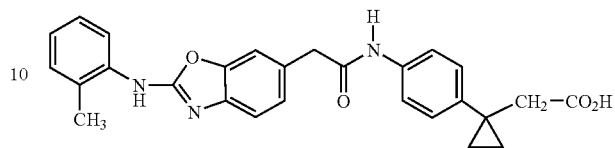

(1-(4-[2-o-Tolylamino-benzoxazol-6-yl]-acetylamino)-phenyl)-cycloprop-1-yl)-acetic acid tert-butyl ester [0.3 g, Reference Example 1(b)] was treated with a mixture of trifluoroacetic acid (10 mL), dichloromethane (2.5 mL) and water (1.5 mL). The resulting cloudy solution was stirred at room temperature and under argon for 1.5 hours. The reaction mixture was evaporated and the residue was chased with toluene (15 mL) and dichloromethane (15 mL) to yield fawn foam (0.29 g) which was recrystallised from a mixture of acetonitrile and water (~30 mL, 9:1, v/v) to give the title compound (0.08 g) as a white solid. LC-MS: $R_T$=3.32 minutes, MS(ES$^+$): 456(M+H)$^+$.

EXAMPLE 9

(1-{4-[2-[2-o-Tolylamino-benzoxazol-6-yl]-acetylamino)-phenyl}-cyclobutyl)-acetic acid

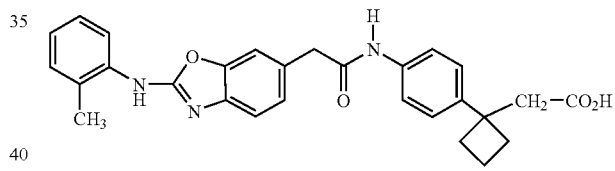

(1-(4-[2-o-Tolylamino-benzoxazol-6-yl]-acetylamino)-phenyl)-cyclobutyl)-acetic acid tert-butyl ester [0.88 g, Reference Example 1(c)] was treated with a mixture of trifluoroacetic acid (30 mL), dichloromethane (7.5 mL) and water (4.5 mL). The resulting amber solution was stirred at room temperature, under argon, for 2.5 hours. The reaction mixture was evaporated and the residue was chased with toluene (25 mL) and dichloromethane (25 mL) to give the title compound (0.73 g) as a fawn foam. LC-MS: $R_T$=3.52 minutes, MS(ES$^+$): 470(M+H)$^+$.

EXAMPLE 10

[1-{4-[2-[4-methyl-2-o-tolylamino-benzoxazol-6-yl]-acetylamino]-phenyl}-cyclopentyl]-acetic acid

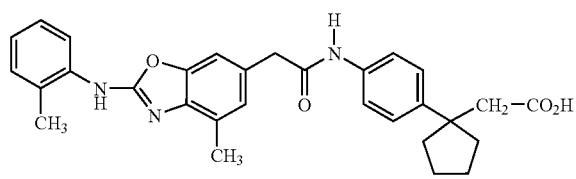

[1-{4-[2-[4-Methyl-2-o-tolylamino-benzoxazol-6-yl]-acetylamino]-phenyl}-cyclopentyl]-acetic acid tert-butyl ester [0.065 g, Reference Example 1(d)] was treated with a mixture of trifluoroacetic acid (2.2 mL), dichloromethane (0.5 mL) and water (0.25 mL). The resultant solution was stirred at room temperature, under argon, for 1.5 hours and then the colourless solution was evaporated. The residue was chased twice with toluene (15 mL) to yield a clear gum. This gum was triturated with pentane and the solid obtained was washed with pentane and then dried at 60° C., under vacuum, to give the title compound (0.25 g) as an off-white solid, m.p. softens at 110° C. then slowly melts from 120–150° C.

EXAMPLE 11

[1-{4-[{2-[3-Methoxy-4-[3-o-tolyl-ureido]-phenyl]-acetyl}-methyl-amino]-phenyl}-cyclopentyl]-acetic acid

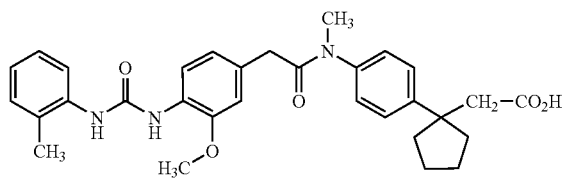

[1-{4-[{2-[3-Methoxy-4-[3-o-tolyl-ureido]-phenyl]-acetyl}-methyl-amino]-phenyl}-cyclopentyl]-acetic acid tert-butyl ester [0.18 g, Reference Example 8(b)] was treated with a mixture of trifluoroacetic acid (6 mL), dichloromethane (1.2 mL) and water (0.75 mL)and the resulting solution was then stirred at room temperature, under argon, for 1.5 hours. The amber coloured reaction mixture was evaporated and the residue was chased twice with toluene (20 mL) to yield an amber gum. This gum was triturated with pentane and the solid obtained was washed with pentane and then dried at 60° C., under vacuum, to give the title compound (0.13 g) as a pale yellow solid, m.p. softens at 100° C. then slowly melts from 118–150° C.

REFERENCE EXAMPLE 1

(a) [1-{4-[2-[2-o-Tolylamino-benzoxazol-6-yl]-acetylamino]-phenyl}-cyclopentyl]-acetic acid tert-butyl ester A stirred solution of [2-(o-tolylamino)-benzoxazol-6-yl]-acetic acid (0.34 g, Reference Example 2) in dry dimethylformamide (22 mL), under argon, was treated with O-(7-azabenzotriazol-1-yl)-1,1,3,3-tetramethyluronium hexafluorophosphate (0.47 g). This solution was stirred at room temperature for 10 minutes and then treated with diisopropylethylamine (0.42 mL) and a solution of [1-(4-amino-phenyl)-cyclopentyl]-acetic acid tert-butyl ester [0.31 g, Reference Example 5(a)] in dry dimethylformamide (8 mL). The resulting amber coloured solution was stirred at room temperature for 1 hour and then evaporated to low bulk. The residue was partitioned between water (containing 1 mL of 1M hydrochloric acid solution) and ethyl acetate. The organic phase was washed with water, then with brine, then dried over magnesium sulfate and then evaporated. The residual pale yellow solid was subjected to flash chromatography on silica eluting with a mixture of dichloromethane and methanol (99:1, v/v) to yield a fawn coloured solid which was recrystallised from ethyl acetate to give the title compound (0.38 g) as an off white solid. MS(ES$^+$): 562.8 (M+Na)$^+$; MS(ES$^-$): 538.4(M−H).

(b) By proceeding in a similar manner to Reference Example 1 (a) but using a mixture of [1-(2-amino-phenyl)-cyclopropyl]-acetic acid tert-butyl ester and [1-(4-amino-phenyl)-cyclopropyl]-acetic acid tert-butyl ester [Reference Example 5(b)] and subjecting the crude reaction product to flash chromatography on silica [eluting initially with a mixture of dichloromethane and methanol (99:1, v/v) and then with a mixture of dichloromethane and methanol (49:1, v/v)] followed by preparative HPLC [on a Hypersil Elite column using as the mobile phase a mixture of acetonitrile, water and trifluoroacetic acid (40:60:0.1, v/v/v) followed by a 1% acetonitrile/minute gradient] there was prepared (1-(4-[2-o-tolylamino-benzoxazol-6-yl]-acetylamino)-phenyl)-cycloprop-1-yl)-acetic acid tert-butyl ester as a pale yellow foam. LC-MS: R$_T$=4.1 minutes, MS(ES$^+$): 512(M+H)$^+$.

(c) By proceeding in a similar manner to Reference Example 1(a) but using [1-(4-amino-phenyl)-cyclobutyl]-acetic acid tert-butyl ester [Reference Example 5(c)] and subjecting the crude reaction product to flash chromatography on silica [eluting initially with a mixture of dichloromethane and methanol (99:1, v/v) and then with a mixture of dichloromethane and methanol (49:1, v/v)] followed by preparative HPLC [on a Hypersil Elite column using as the mobile phase a mixture of acetonitrile, water and trifluoroacetic acid (45:55:0.1, v/v/v) followed by a 1% acetonitrile/minute gradient] there was prepared (1-(4-[2-o-tolylamino-benzoxazol-6-yl]-acetylamino)-phenyl)-cyclobutyl)-acetic acid tert-butyl ester as a pale amber gum. LC-MS: R$_T$=4.3 minutes, MS(ES$^+$): 526(M+H)$^+$.

(d) By proceeding in a similar manner to Reference Example 1 (a) but using (4-methyl-2-o-tolylamino-benzoxazol-6-yl)-acetic acid [0.44 g, prepared according to the procedure described in International Patent Application No. WO00/61580 for Reference Example 9] and subjecting the crude reaction product to flash chromatography on silica [eluting initially with a mixture of cyclohexane and ethyl acetate (5:1, v/v) and then with a mixture of cyclohexane and ethyl acetate (3:1, v/v)] followed by recrystallisation from ethyl acetate there was prepared [1-{4-[2-[4-methyl-2-o-tolylamino-benzoxazol-6-yl]-acetylamino]-phenyl}-cyclopentyl]-acetic acid tert-butyl ester as an off-white solid. MS(ES$^+$): 554(M+H)$^+$.

REFERENCE EXAMPLE 2

(2-o-Tolylamino-benzoxazol-6-yl)-acetic acid

A mixture of (4-amino-3-hydroxy-phenyl)-acetic acid ethyl ester (3.3 g, Reference Example 3) and o-tolylisothiocyanate (2.5 mL) in ethanol (150 mL) was stirred at room temperature for about 2 hours. After standing at room temperature overnight the mixture was evaporated and the residue was subjected to flash chromatography on silica eluting with a mixture of pentane and ethyl acetate (7:3, v/v) to give a yellow foam. A solution of this material in ethanol (150 mL) was treated with dicyclohexylcarbodiimide (3.0 g) and the mixture was heated at reflux temperature for 2 hours. The mixture was evaporated and the residue subjected to short column chromatography (on silica eluting with a mixture of tert-butyl methyl ether and dichloromethane, 1:19 to 1:9 v/v). The resulting light yellow oil was dissolved in ethanol (100 mL) and the solution was treated with sodium hydroxide solution (15 mL, 1M) then heated at reflux temperature for 2 hours. The reaction mixture was evaporated and the residue was dissolved in water. The solution was washed with ethyl acetate and the aqueous layer was acidified to pH 1 by addition of concentrated hydrochloric acid. The resulting white precipitate was collected by filtration, then washed thoroughly with water, and then dried to give the title compound (1.8 g) as a white solid.

REFERENCE EXAMPLE 3

(4-Amino-3-hydroxy-phenyl)-acetic acid ethyl ester

A solution of (3-hydroxy-4-nitro-phenyl)-acetic acid ethyl ester (5.0 g, Reference Example 4) was dissolved in ethanol (approximately 200 mL) was treated with ammonium formate (approximately 20 g). The mixture was warmed to 50° C. and then treated cautiously with palladium on charcoal (approximately 1 g, 5%)—effervescence was observed. After 30 minutes the mixture was filtered hot through a pad of filter-aid and the filtrate was concentrated to give the title compound (3.3 g) as a black solid.

REFERENCE EXAMPLE 4

(3-Hydroxy-4-nitro-phenyl)-acetic acid ethyl ester

A solution of (3-hydroxy-4-nitro-phenyl)-acetic acid (4.0 g, prepared according to the procedure described by Meyer et al, J. Med. Chem., 1997, 40, pages 1049–1062) in ethanol (approximately 100 mL) was treated with concentrated hydrochloric acid (5–8 drops) was heated at reflux temperature for 3 hours then evaporated. The residue was dissolved in tert-butyl methyl ether and the solution was washed with saturated aqueous sodium bicarbonate solution, then with water, then dried, and then evaporated to give the title compound (5.0 g) as a light yellow solid.

REFERENCE EXAMPLE 5

(a) [1-(4-Amino-phenyl)-cyclopentyl]-acetic acid tert-butyl ester

A stirred solution of [1-(4-nitro-phenyl)-cyclopentyl]-acetic acid tert-butyl ester [1.0 g, Reference Example 6(a)] in methanol (40 mL) was treated with water (40 mL), ammonium chloride (0.87 g) and iron powder (325 mesh, 0.55 g). The mixture was stirred at gentle reflux for 2.5 hours and then the hot mixture was filtered through hyflo. The filter pad was washed well with methanol. The combined filtrate and washings was evaporated and the residue was partitioned between ethyl acetate and water. The organic phase was dried over magnesium sulfate and then evaporated to give the title compound (0.63 g) as a golden oil.

(b) By proceeding in a similar manner to Reference Example 5(a) but using a mixture of [1-(2-nitro-phenyl)-cyclopropyl]-acetic acid tert-butyl ester [1-(4-nitro-phenyl)-cyclopropyl]-acetic acid tert-butyl ester [Reference Example 6(b)] there was prepared a mixture of [1-(2-amino-phenyl)-cyclopropyl]-acetic acid tert-butyl ester and [1-(4-amino-phenyl)-cyclopropyl]-acetic acid tert-butyl ester as a yellow oil. LC-MS: $R_T$=2.39 minutes, MS(ES$^+$): 248(M+H)$^+$.

(c) By proceeding in a similar manner to Reference Example 5(a) but using [1-(4-nitro-phenyl)-cyclobutyl]-acetic acid tert-butyl ester [Reference Example 6(c)] there was prepared [1-(4-amino-phenyl)-cyclobutyl]-acetic acid tert-butyl ester as an amber oil. LC-MS: $R_T$=2.91 minutes, MS(ES$^+$): 262(M+H)$^+$.

REFERENCE EXAMPLE 6

(a) [1-(4-Nitro-phenyl)-cyclopentyl]-acetic acid tert-butyl ester

A stirred solution of (trimethylsilyl) diazomethane in hexanes (25 mL, 2.0 M) in dry acetonitrile (75 mL), at 0° C. and under argon, was treated dropwise with a solution of 1-(4-nitro-phenyl)-cyclopentanecarbonyl chloride [9.5 g, Reference Example 7(a)] in dry acetonitrile (50 mL) over 2 minutes. The cooling bath was removed and the solution was stirred at room temperature for 2 hours and then evaporated. The residue was partitioned between ethyl acetate and aqueous sodium bicarbonate solution. The organic layer washed with brine, then dried over magnesium sulfate and then evaporated. The resulting amber coloured oil was dissolved in 2-methyl-2-propanol (100 mL) and this solution was stirred, heated to gentle reflux and then treated dropwise with a solution of silver benzoate (5.0 g) in triethylamine (35 mL) over 1 minute (nitrogen was evolved). The resulting dark coloured mixture was stirred at gentle reflux for 2.5 hours and then the hot mixture was filtered through hyflo. The filtrate was evaporated and the residue was partitioned between ethyl acetate and water. The organic layer was washed with aqueous sodium bicarbonate solution, then with water, then with 1M aqueous hydrochloric acid solution, then with water, then with aqueous sodium bicarbonate solution, then with brine, then dried over magnesium sulfate and then evaporated. The residual black oil was subjected to flash chromatography on silica eluting with a mixture of cyclohexane and ethyl acetate (30:1, v/v) to give a waxy white gum, which was treated with pentane, and a white solid removed by filtration. The filtrate was evaporated to give the title compound (2.68 g) as a yellow oil.

(b) By proceeding in a similar manner to Reference Example 6(a) but using a mixture of 1-(2-nitro-phenyl)-cyclopropanecarbonyl chloride and 1-(4-nitro-phenyl)-cyclopropanecarbonyl chloride [Reference Example 7(b)] and subjecting the material obtained after flash chromatography to preparative HPLC on a Hypersil Elite column using as the mobile phase a mixture of acetonitrile, water and trifluoroacetic acid (45:55:0.1, v/v/v) followed by a 1% acetonitrile/minute gradient there was prepared a mixture of [1-(2-nitro-phenyl)-cyclopropyl]-acetic acid tert-butyl ester and [1-(4-nitro-phenyl)-cyclopropyl]-acetic acid tert-butyl ester as a colourless oil. LC-MS: $R_T$=4.08 minutes, MS(ES$^+$): very weak 278(M+H)$^+$.

(c) By proceeding in a similar manner to Reference Example 6(a) but using 1-(4-nitro-phenyl)-cyclobutanecarbonyl chloride [Reference Example 7(c)] there was prepared [1-(4-nitro-phenyl)-cyclobutyl]-acetic acid tert-butyl ester. LC-MS: $R_T$=4.35 minutes.

REFERENCE EXAMPLE 7

(a) 1-(4-Nitro-phenyl)-cyclopentanecarbonyl chloride

A stirred suspension of 1-(4-nitro-phenyl)-cyclopentanecarboxylic acid (8.85 g) in dry dichloromethane (100 mL) was treated with oxalyl chloride (5.0 mL) and catalytic amount dry dimethylformamide (5 drops). The mixture was stirred at room temperature, under anhydrous conditions, for 16 hours then evaporated to give the title compound as an off white solid (100%), which was used without further purification.

(b) By proceeding in a similar manner to Reference Example 7(a) but using a mixture of 1-(2-nitro-phenyl)-cyclopropanecarboxylic acid and 1-(4-nitro-phenyl)-cyclopropanecarboxylic acid [Reference Example 25(a)] there was prepared a mixture of 1-(2-nitro-phenyl)-cyclopropanecarbonyl chloride and 1-(4-nitro-phenyl)-cyclopropanecarbonyl chloride as an amber oil, which was used without further purification.

(c) By proceeding in a similar manner to Reference Example 7(a) but using 1-(2-nitro-phenyl)-cyclopropanecarboxylic acid [Reference Example 25(b)] there was prepared 1-(2-nitro-phenyl)-cyclobutanecarbonyl chloride as a pale amber waxy solid.

REFERENCE EXAMPLE 8

[1-{4-[2-[3-Methoxy-4-[3-o-tolyl-ureido]-phenyl]-acetylamino]-phenyl}-cyclopentyl]-acetic acid tert-butyl ester A stirred solution of [3-methoxy-4-(3-o-tolyl-ureido)-phenyl]-acetic acid (0.26 g, prepared as described in Example 52 of International Patent Application Publication No. WO 96/22966) in dry dimethylformamide (15 mL), under argon, was treated with O-(7-azabenzotriazol-1-yl)-1,1,3,3-tetramethyluronium hexafluorophosphate (0.32 g). This solution was stirred at room temperature for 10 minutes and then treated with diisopropylethylamine (0.28 ml) and a solution of [1-(4-amino-phenyl)-cyclopentyl]-acetic acid tert-butyl ester (0.21 g, Reference Example 5a) in dry dimethylformamide (5 mL). The resulting amber coloured solution was stirred at room temperature for 2 hours and then evaporated to low bulk. The residue was partitioned between water (containing 1 mL of 1M hydrochloric acid solution) and ethyl acetate. The organic phase was washed with water, then with brine, then dried over magnesium sulfate and then evaporated to yield a fawn solid which was subjected to flash chromatography on silica eluting with a mixture of dichloromethane and methanol (49:1, v/v) to give the title compound (0.30 g) as a pale yellow solid. MS(ES$^+$): 594(M+Na)$^+$; MS (ES$^-$): 570 (M−H).

(b) By proceeding in a similar manner to Reference Example 8(a) but using [1-(4-N-methylamino-phenyl)-cyclopentyl]-acetic acid tert-butyl ester (Reference Example 27) and subjecting the crude reaction product to flash chromatography on silica [eluting initially with a mixture of cyclohexane and ethyl acetate (2:1, v/v) and then with a mixture of cyclohexane and ethyl acetate (1:1, v/v)] there was prepared [1-{4-[{2-[3-methoxy-4-[3-o-tolyl-ureido]-phenyl]-acetyl}-methyl-amino]-phenyl}-cyclopentyl]-acetic acid tert-butyl ester as a yellow foam.

REFERENCE EXAMPLE 9

(a) (2-(4-(2-(2-o-Tolylamino-benzoxazol-6-yl)-acetylamino)-phenyl)-indan-2: yl)-acetic acid ethyl ester A solution of (2-o-tolylamino-benzoxazol-6-yl)-acetic acid (0.25 g, Reference Example 2) in dimethylformamide (3 mL) was treated with O-(7-azabenzotriazol-1-yl)-1,1,3,3-tetramethyluronium hexafluorophosphate (0.368 g) and diisopropylethylamine (0.613 μL) in dimethylformamide (3 mL) and then with a solution of [2-(4-amino-phenyl)-indan-2-yl]-acetic acid ethyl ester (0.259 g, Reference Example 10) in dimethylformamide (5 mL). After stirring at room temperature overnight the reaction mixture was evaporated. The residue was treated with water and this mixture was extracted with ethyl acetate. The ethyl acetate extracts was washed with hydrochloric acid (0.5N), then with saturated aqueous sodium hydrogen carbonate, then dried over magnesium sulfate and then evaporated. The residue was subjected to chromatography [HPLC using 50% acetonitrile-water with a flow rate of 1 ml/minute] to give the title compound (0.397 g).

(b) By proceeding in a similar manner to Reference Example 9(a) but using [2-(4-amino-phenyl)-indan-1-yl]-acetic acid methyl ester (Reference Example 24) and subjecting the crude reaction product to flash chromatography on silica eluting initially with a mixture of cyclohexane and ethyl acetate (3:1, v/v) and then with a mixture of cyclohexane and ethyl acetate (2:1, v/v) there was prepared (1-{4-[2-(2-o-tolylamino-benzoxazol-6-yl)-acetylamino]-phenyl}-indan-1-yl)-acetic acid methyl ester as a yellow foam. LC-MS: R$_T$=4.08 minutes, MS(ES$^+$): 546(M+H)$^+$.

REFERENCE EXAMPLE 10

[2-(4-Amino-phenyl)-indan-2-yl]-acetic acid ethyl ester

A mixture of [2-(4-acetylamino-phenyl)-indan-2-yl]-acetic acid ethyl ester (0.296 g, Reference Example 11) and hydrochloric acid (60 mL, 6N) was heated at gentle reflux for 3 hours then evaporated. The residue was treated with ethanol (80 mL) and this mixture was heated at reflux temperature for 3 hours then left at room temperature overnight and then evaporated to give the title compound as a dark coloured solid which was used without further purification.

REFERENCE EXAMPLE 11

[2-(4-Acetylamino-phenyl)-indan-2-yl]-acetic acid ethyl ester

A stirred solution of [2-(4-acetylamino-phenyl)-1,3-dihydroxy-indan-2-yl]-acetic acid ethyl ester (0.38 g, Reference Example 12) in acetic acid (20 mL), under nitrogen, was treated with palladium black (20 mg), then the flask was evacuated and then hydrogen was introduced into the flask via a balloon. After stirring at 50° C. for 2 days the reaction mixture was filtered through Hi-flow supercel. The filtrate was concentrated then diluted with ethyl acetate (100 mL). This solution was washed with saturated sodium hydrogen carbonate solution (100 mL), then with water (100 mL), then dried over magnesium sulfate and then evaporated to give the title compound (0.296 g) as an amber coloured gum.

REFERENCE EXAMPLE 12

[2-(4-acetylamino-phenyl)-1,3-dihydroxy-indan-2-yl]-acetic acid ethyl ester

A stirred solution of [2-(4-acetylamino-phenyl)-1,3-dioxo-indan-2-yl]-acetic acid ethyl ester (4.0 g, Reference Example 13) in absolute ethanol (250 mL) was treated portionwise with sodium borohydride (1.7 g). After stirring at room temperature for 4 hours the reaction mixture was treated with glacial acetic acid until pH 7 and then evaporated. The residue was treated with water (100 mL) and the mixture was extracted with ethyl acetate (150 mL). The organic extract was dried over magnesium sulfate and then evaporated. The residue was subjected to chromatography

REFERENCE EXAMPLE 13

2-(4-acetylaminophenyl)-1,3-dioxo-indan-2-yl-acetic acid ethyl ester

A solution of sodium (0.412 g) in absolute ethanol ((200 mL) was treated with 2-(4-acetylaminophenyl)-indan-1,3-dione (5 g, Reference Example 14) then with sodium iodide (2.69 g) and chloroacetic acid ethyl ester (3.6 mL). The mixture was heated at 100° C. for 20 minutes then poured into water (500 mL) and then extracted with ethyl acetate (500 mL). The organic extract was dried over magnesium sulfate and then evaporated to give the title compound (5.25 g) as a pale coloured solid.

REFERENCE EXAMPLE 14

N-[4-(1,3-Dioxo-indan-2-yl)-phenyl]-acetamide

A mixture of (4-acetylamino-phenyl)-acetic acid (15 g, Reference Example 15) phthallic anhydride (15.8 g) and triethylamine (42.3 mL) was heated at 70° C. for 3 minutes then treated with acetic anhydride (105.8 mL). The mixture was heated on a steam bath at approximately 70° C. until evolution of carbon dioxide ceased. The resulting deep red solution was evaporated and the residue was treated with water (750 mL) then heated on a steam bath for 2 hours. The insoluble material was filtered, dried under vacuum and then subjected to chromatography on silica eluting with mixtures of dichloromethane and methanol (99:5 to 50:50, v/v) to give the title compound.

REFERENCE EXAMPLE 15

(4-acetylamino-phenyl)-acetic acid

A mixture of (4-amino-phenyl)-acetic acid (25 g) in acetic acid (200 mL) was treated with acetic anhydride (31.3 mL). The mixture was heated on a steam bath for 4 hours, then cooled, then treated with water (20 mL) and then evaporated. The residue was dried under vacuum to give the title compound (30.4 g) as a beige coloured solid.

REFERENCE EXAMPLE 16

[2-(4-(2-(3-methoxy-4-(3-o-tolyl-ureido)-phenyl)-acetylamino)-phenyl)-indan-2-yl]-acetic acid ethyl ester A solution of [2-(4-amino-phenyl)-indan-2-yl]-acetic acid ethyl ester (0.158 g, Reference Example 10) in dimethylformamide (2 mL) was treated with a solution of [3-methoxy-4-(3-o-tolyl-ureido)-phenyl]-acetic acid (0.169 g) in dimethylformamide (2 mL) which had been treated with diisopropylethylamine (1.3 mL) and a solution of O-(7-azabenzotriazol-1-yl)-1,1,3,3-tetramethyluronium hexafluorophosphate (0.223 g) in dimethylformamide (2 mL). After stirring at room temperature for 2 hours the reaction mixture was evaporated and the residue was partitioned between ethyl acetate (30 mL) and hydrochloric acid (30 mL, 0.5N). The organic phase was washed with hydrochloric acid (30 mL, 0.5N), then with saturated sodium hydrogen carbonate solution (30 mL), then dried over magnesium sulfate and then evaporated. The residual beige coloured solid was subjected to chromatography on silica eluting with a mixture of ethyl acetate and cyclohexane (2:1, v/v) to give the title compound (0.06 g).

REFERENCE EXAMPLE 17

(a) (4-(4-{2-[4-Methyl-2-o-tolylamino-benzoxazol-6-yl]-acetylamino}-phenyl)-tetrahydro-pyran-4-yl)-acetic acid methyl ester A stirred solution of (4-methyl-2-o-tolylamino-benzoxazol-6-yl)-acetic acid [0.44 g, prepared according to the procedure described in International Patent Application No. WO00/61580 for Reference Example 9] in dry dimethylformamide (10 mL), under argon, was treated with O-(7-azabenzotriazol-1-yl)-1,1,3,3-tetramethyluronium hexafluorophosphate (0.8477 g) and then with diisopropylethylamine (1.05 mL). After stirring at room temperature for 10 minutes the bright yellow solution was added to a solution of [4-{4-amino-phenyl}-tetrahydro-pyran-4-yl]-acetic acid methyl ester trifluoroacetate (0.444 g, Reference Example 18) in a mixture of dimethylformamide (8 mL) and diisopropylethylamine (1.05 mL). The mixture was stirred at room temperature under argon overnight and then evaporated to low bulk. The residue was dissolved in ethyl acetate and this solution was washed with water, then with aqueous sodium bicarbonate solution, and then with water and then evaporated. The residue was subjected to reverse phase HPLC on a Hypersil Elite C18 column using as the mobile phase a mixture of acetonitrile, water and trifluoroacetic acid (35:65:0.1, v/v/v) followed by a 1% acetonitrile/minute gradient to give the title compound (0.178 g, approximately 90% purity) which was used without further purification. LC-MS: $R_T$=3.71 minutes, MS(ES+): 528(M+H)+.

(b) By proceeding in a similar manner to Reference Example 1(a) but using (2-o-tolylamino-benzoxazol-6-yl)-acetic acid [prepared according to the procedure described in International Patent Application No. WO00/61580 for Reference Example 2] there was prepared (4-(4-{2-[2-o-tolylamino-benzoxazol-6-yl]-acetylamino}-phenyl)-tetrahydro-pyran-4-yl)-acetic acid methyl ester as an off-white glassy solid. LC-MS: $R_T$=3.45 minutes, MS(ES$^+$): 514(M+H)$^+$. This material which was shown to contain a small amount of the corresponding ethyl ester, MS(ES$^+$): 528 (M+H)$^+$, was used without further purification.

REFERENCE EXAMPLE 18

[4-{4-Amino-phenyl}-tetrahydro-pyran-4-yl]-acetic acid methyl ester trifluoroacetate (4-{4-Benzhydryl-amino)-phenyl}-tetrahydro-pyran-4-yl)-acetic acid methyl ester [2.1 g, Reference Example 19(a)] was treated with a mixture of trifluoroacetic acid and water (15 mL, 19:1, v/v). The resulting cloudy solution was stirred under argon and at room temperature for 22.5 hours then treated further with a mixture of trifluoroacetic acid and water (10 mL, 9:1, v/v). This mixture was heated at 50° C. under argon for 2 hours then evaporated. The residue was kept under high vacuum for 2 hours to give the title compound (3.28 g) as a black gum. LC-MS: $R_T$=0.36 minutes, MS(ES$^+$): 250(M+H)$^+$. This material was used immediately without further purification.

REFERENCE EXAMPLE 19

(a) (4-{4-Benzhydryl-amino)-phenyl}-tetrahydro-pyran-4-yl)-acetic acid methyl ester A solution of (4-{4-chloro-phenyl}-tetrahydro-pyran-4-yl)-acetic acid methyl ester [1.5 g, Reference Example 20(a)] in dry toluene (120 mL) was degassed with argon, then treated with palladium (II) acetate (0.135 g) followed by 2-(di-t-butylphosphino)biphenyl (0.18 g), aminodiphenylmethane (1.28 g) and sodium tert-butoxide (0.75 g). The resulting dark solution was stirred at 80° C., under argon, for 20 hours, then treated with ethyl acetate (10 mL) and water (5 mL). The organic phase was separated, then dried over magnesium sulfate and then evaporated. The residual dark oil (3.38 g) was subjected to flash chromatography on silica eluting initially with a mixture of cyclohexane and ethyl acetate (5:1, v/v) and then with a mixture of cyclohexane and ethyl acetate (3:1, v/v) to give the title compound (1.03 g) as a clear gum. LC-MS: $R_T$=4.16 minutes, MS(ES$^+$): 416 and 414(M+H)$^+$.

(b) By proceeding in a similar manner to Reference Example 19(a) but using [1-(4-chlorophenyl)-indan-1-yl]-acetic acid methyl ester [Reference Example 20(b)] there was prepared [1-(4-(benzhydryl-amino)-phenyl)-indan-1-yl]-acetic acid methyl ester as an amber gum. LC-MS: $R_T$=4.72 minutes, MS(ES$^+$): 448(M+H)$^+$.

REFERENCE EXAMPLE 20

(a) (4-{4-chloro-phenyl}-tetrahydro-pyran-4-yl)-acetic acid methyl ester

A stirred solution of (4-{4-chloro-phenyl}-tetrahydro-pyran-4-yl)-acetic acid [3.3 g, Reference Example 21(a)] in anhydrous methanol (125 mL), under argon, was treated with concentrated sulfuric acid (8 drops). This mixture was stirred at reflux temperature for 5.5 hours then evaporated. The residue was treated with ethyl acetate (35 mL) and the resulting solution was washed three times with water (10 mL), then dried over magnesium sulfate and then evaporated to give the title compound (3.12 g) as a pale amber oil. LC-MS: $R_T$=3.43 minutes, MS(ES$^+$): 269 and 271(M+H)$^+$.

(b) By proceeding in a similar manner to Reference Example 20(a) but using [1-(4-chloro-phenyl)-indan-1-yl]-acetic acid [Reference Example 21(b)] there was prepared [1-(4-chloro-phenyl)-indan-1-yl]-acetic acid methyl ester as a red oil. LC-MS: $R_T$=4.39 minutes.

REFERENCE EXAMPLE 21

(a) (4-{4-Chloro-phenyl}-tetrahydro-pyran-4-yl)-acetic acid

A stirred solution of (4-{4-chloro-phenyl}-tetrahydro-pyran-4-yl)-cyano-acetic acid ethyl ester (3.3 g, Reference Example 22) in ethylene glycol (50 mL) was treated with a solution of potassium hydroxide (5 g) in water (10 mL) in one portion and then heated at reflux temperature for 23 hours. The resultant pale amber solution was evaporated and the oily residue was treated with water (50 mL). The mixture was washed with diethyl ether (20 mL), then ice-cooled, then acidified to pH 1 by addition of concentrated hydrochloric acid (3 mL) and then extracted with diethyl ether (50 mL). The organic extract was washed with water (25 mL) then dried over magnesium sulfate and then evaporated to give the title compound (3.42 g) as a colourless oil, which slowly crystallised on standing. LC-MS: $R_T$=2.92 minutes, MS(ES$^+$): 253 and 255(M+H)$^+$.

(b) By proceeding in a similar manner to Reference Example 21 (a) but using [1-(4-chloro-phenyl)-indan-1-yl]-cyano-acetic acid ethyl ester [Reference Example 22(b)] there was prepared [1-(4-chlorophenyl)-indan-1-yl]-acetic acid as a colourless oil. LC-MS: $R_T$=4.28 minutes, MS(ES$^-$): 338 and 340(M–H)$^-$.

REFERENCE EXAMPLE 22

(a) (4-{4-chloro-phenyl}-tetrahydro-pyran-4-yl)-cyano-acetic acid ethyl ester A stirred mixture of cyano-(tetrahydro-pyran-4-ylidene)-acetic acid ethyl ester (3.9 g, Reference Example 23(a)) in dry diethyl ether (60 mL), under nitrogen, was treated dropwise over 20 minutes with a solution of 4-chlorophenylmagnesium bromide in diethyl ether (25 mL, 1M). An off-white solid was precipitated and there was a slight exotherm. This thick suspension was stirred at gentle reflux for 2.5 hours, then ice-cooled and then treated with hydrochloric acid (10 mL, 1N) followed by ethyl acetate (20 mL). The organic phase was separated, then dried over magnesium sulfate and then evaporated to give a pale yellow oil (7.86 g) which was subjected to flash chromatography on silica eluting initially with a mixture of cyclohexane and ethyl acetate (8:1, v/v) and then with a mixture of cyclohexane and ethyl acetate (5:1, v/v) to give the title compound (4.46 g) as a colourless oil. LC-MS: $R_T$=3.54 minutes, MS(ES$^+$): 308 and 310(M+H)$^+$, MS(ES$^-$): 306 and 308(M–H)$^-$.

(b) By proceeding in a similar manner to Reference Example 22(a) but using cyano-indan-1-ylidene-acetic acid ethyl ester [Reference Example 23(b)] there was prepared [1-(4-chloro-phenyl)-indan-1-yl]-cyano-acetic acid ethyl ester LC-MS: $R_T$=4.28 minutes, MS(ES–): 338 and 340(M–H)–.

REFERENCE EXAMPLE 23

(a) Cyano-(tetrahydro-pyran-4-ylidene)-acetic acid ethyl ester

A stirred solution of tetrahydro-pyran-4-one (5 g) in toluene (50 mL) was treated sequentially with cyano-acetic acid ethyl ester (5.3 mL), ammonium acetate (0.7 g), acetic acid (2.2 mL) and piperidine (3 drops) then stirred at reflux temperature for 3.5 hours and then stood at room temperature for 3 days. The reaction mixture was evaporated to give a red oil, which solidified on standing at room temperature. This solid was treated with water (30 mL) and the mixture was extracted with ethyl acetate (50 mL). The extract was washed with saturated aqueous sodium bicarbonate solution (30 mL), then with water (30 mL), then dried over magnesium sulfate and then evaporated. The residual pale yellow waxy solid (8.92 g) was refluxed with petroleum ether (b.p. 80–100° C.) when partial solution was achieved. This mixture was treated with cyclohexane (20 mL) and then decanted to remove a small amount of brown gum. The decanted solution was stood at room temperature overnight and the resulting crystalline pale yellow solid was filtered then washed with pentane and then dried at 40° C. under vacuum to give the title compound (5.10 g) as a pale yellow crystalline solid. LC-MS: $R_T$=2.85 minutes, MS(ES$^+$): 169 (M+H)$^+$, MS(ES$^-$): 194(M–H)$^-$.

(b) By proceeding in a similar manner to Reference Example 23(a) but using 1-indanone the re was prepared 2-cyano-2-(indan-1-ylidene)-acetic acid ethyl ester as an off-white solid. LC-MS: $R_T$=3.28 minutes, MS(ES⁻): 226 (M−H)⁻.

REFERENCE EXAMPLE 24

[1-(4-amino-phenyl)-indan-1-yl]-acetic acid methyl ester

[1-(4-(Benzhydryl-amino)-phenyl)-indan-1-yl]-acetic acid methyl ester [(0.15 g, Reference Example 19(b)] was treated with a mixture of trifluoroacetic acid (9 mL) and water (1 mL). The resulting deep red solution was stirred at 50° C., under argon, for 2 hours and then evaporated. The residue was chased with toluene (25 mL) and then placed under vacuum to give the title compound (0.19 g) as a red gum. LC-MS: $R_T$=2.54 minutes, MS(ES⁺): 282(M+H)⁺. This material was used immediately for the preparation of Reference Example 9(b).

REFERENCE EXAMPLE 25

(a) 1-(4-Nitro-phenyl)-cyclopropanecarboxylic acid

A stirred solution of fuming nitric acid (1.6 mL), at −30° C. and under nitrogen, was treated portionwise with 1-phenyl-cyclopropanecarboxylic acid (10 g). The reaction mixture was allowed to warm to 0° C., then stirred at this temperature for 2 hours and then poured into ice(100 g). The resulting solid was filtered, then washed well with water, then dried at 60° C. under vacuo and then recrystallised from toluene to give 1-(2-nitro-phenyl)-cyclopropanecarboxylic acid and 1-(4-nitro-phenyl)-cyclopropanecarboxylic acid (11.35 g). MS(ES⁻): 206 (M−H)⁻.

(b) By proceeding in a similar manner to Reference Example 25(a) but using 1-phenyl-cyclobutanecarboxylic acid (Reference Example 26) there was prepared 1-(2-nitrophenyl)-cyclobutanecarboxylic acid as a pale amber waxy solid. MS(ES⁻): 220(M−H)⁻.

REFERENCE EXAMPLE 26

1-phenyl-cyclobutanecarboxylic acid

A stirred suspension of palladium on carbon (3.6 g, 5%) in isopropanol (200 mL) was treated in one portion with a solution of ammonium formate (9 g) in water (12.5 mL) followed by a solution of 1-(4-chloro-phenyl)-cyclobutanecarboxylic acid (15 g) in isopropanol (150 mL) also in one portion. The resultant suspension was stirred at 65° C. for 30 minutes and then treated with a further aliquot of a solution of ammonium formate (9 g) in water (12.5 mL). After stirring at 65° C. for a further 4.5 hours the reaction mixture was filtered through Hyflo and the filter pad was washed three times with isopropanol (75 mL). The combined filtrate and washings were evaporated. The solid obtained after standing at room temperature for 3 days was treated with ethyl acetate (350 mL) and water (150 mL) and the organic phase was separated, then dried over magnesium sulfate and then evaporated to give the title compound (9.25 g) as a white solid. LC-MS: $R_T$=3.08 minutes, MS(ES⁺): very weak 177(M+H)⁺.

REFERENCE EXAMPLE 27

[1-(4-Methylamino-phenyl)-cyclopentyl]-acetic acid tert-butyl ester

A stirred suspension of [1-(4-{(benzotriazol-1-ylmethyl)-amino}-phenyl)-cyclopentyl]-acetic acid tert-butyl ester (0.21 g) in ethanol (10 mL), under argon, was treated with sodium borohydride (0.051 g). After stirring at room temperature for 2 hours a further aliquot of sodium borohydride (0.017 g) was added and stirring was continued for a further hour, then a further aliquot of sodium borohydride (0.017 g) was added and stirring was continued for a further hour. The reaction mixture was then evaporated and the residue was treated with water (15 mL) and ethyl acetate (25 mL). The organic phase was separated and then washed with water (15 mL), then with brine (15 mL), then dried over magnesium sulfate and then evaporated to give the title compound (0.15 g) as an amber oil which crystallised on standing.

In Vitro and In Vivo Test Procedures

1. Inhibitory Effects of Compounds on VLA4 Dependent Cell Adhesion to Fibronectin and VCAM.

1.1 Metabolic Labelling of RAMOS Cells.

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 μCi/ 100 mls of [³H]-methionine (Amersham, UK) for 18 hours at 37° C.

1.2 96 Well Plate Preparation for Adhesion Assay.

Cytostar plates (Amersham, UK) were coated with 50 μl/well of either 3 μg/ml human soluble VCAM-1 (R&D Systems Ltd, UK) or 28.8 μg/ml human tissue Fibronectin (Sigma, UK). In control non-specific binding wells 50 μl phosphate buffered saline was added. The plates were then left to dry in an incubator at 25° C., overnight. The next day the plates were blocked with 200 μl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 μl/well of 3.6% dimethyl sulfoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 μl/well of the test compounds at the appropriate concentrations diluted in 3.6% dimethyl sulfoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 50 μl/well of cells in 3.6% dimethyl sulfoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis.

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an $IC_{50}$, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ is the counts bound to fibronectin (or VCAM-1) coated wells without inhibitor present, $C_{NS}$ is the counts present in wells without substrate, and $C_I$ are the counts present in wells containing a cell adhesion inhibitor.

Compound data of this invention is expressed for $IC_{50}$s for inhibition of cell adhesion to both fibronectin and VCAM-1. Compounds of the invention inhibit cell adhesion to fibronectin and VCAM-1 with $IC_{50}$'s in the range 100 micromolar to 1 nanomolar.

2. Inhibition of Antigen-induced Airway Inflammation in the Mouse and Rat.

2.1 Sensitization of the Animals.

Rats (Brown Norway, Harland Olac, UK) are sensitized on days 0, 12 and 21 with ovalbumin (100 μg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 μg, i.p.) administered with aluminium hydroxide adjuvant (20 mg, i.p.) in saline (0.2 ml, i.p.).

2.2 Antigen Challenge.

Rats are challenged on any one day between days 28–38, while mice are challenged on any one day between days 20–30.

The animals are challenged by exposure for 30 minutes (rats) or 1 hour (mice) to an aerosol of ovalbumin (10 g/l) generated by an ultrasonic nebulizer (deVilbiss Ultraneb, US) and passed into an exposure chamber.

2.3 Treatment Protocols.

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or, 0.5 mg/kg i.t.; for mice 10 ml/kg, p.o. or 1 ml/kg, i.t.

2.4 Assessment of Airway Inflammation.

The cell accumulation in the lung is assessed 24 hours after challenge (rats) or 48–72 hours after challenge (mice). The animals are euthanized with sodium pentobarbitone. (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK)

2.5 Data Analysis.

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where $p<0.05$, no statistical significance existed.

What is claimed is:

1. A compound of formula (Ib):

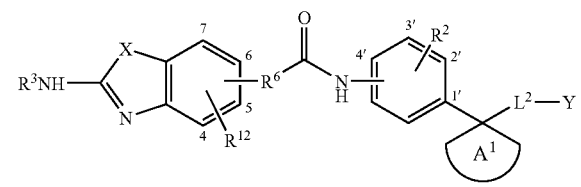

(Ib)

wherein:

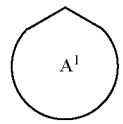

is (i) a saturated 3- to 6-membered carbocycle, optionally substituted by one or more alkyl groups, (ii) indanyl or (iii) a saturated 4- to 6-membered heterocyclic ring;

$R^2$ is hydrogen, halogen, lower alkyl or lower alkoxy;

$R^3$ is an optionally substituted aryl or optionally substituted heteroaryl;

$R^6$ is a direct bond or a straight or branched alkylene chain, alkenylene chain or alkynylene chain;

$L^2$ is an alkylene linkage;

Y is carboxy;

X is O;

and $R^{12}$ is hydrogen or an aryl group substituent;

and the corresponding N-oxides and ester prodrugs of such compounds; and pharmaceutically acceptable salts and solvates of such compounds and their N-oxides and ester prodrugs.

2. A compound according to claim 1 in which

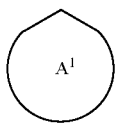

represents a saturated 3- to 6-membered carbocycle optionally substituted by one or more alkyl groups.

3. A compound according to claim 2 in which

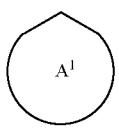

represents cyclopropyl, cyclobutyl, cyclopentyl or 3,3-dimethylcyclopentyl.

4. A compound according to claim 1 in which

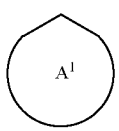

represents indanyl.

5. A compound according to claim 1 in which

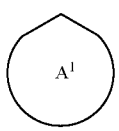

represents a 4- to 6-membered heterocyclic ring in which the hetero entity is selected from O, S, SO$_2$, or NY$^5$, where Y$^5$ is hydrogen, alkyl, aryl, arylalkyl, —C(=O)—R, —C(=O)—OR or —SO$_2$R and R is alky, aryl, arylalkyl, cycloalkyl, cycloalkylalkyl, heteroaryl, heteroarylalkyl, heterocycloalkyl or heterocycloalkylalkyl.

6. A compound according to claim 5 in which

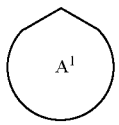

represents a 6-membered heterocyclic ring in which the hetero entity is O or NY$^5$, where Y$^5$ is hydrogen, alkyl, or —C(=O)-alkyl.

7. A compound according to claim 1 in which

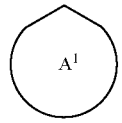

represents

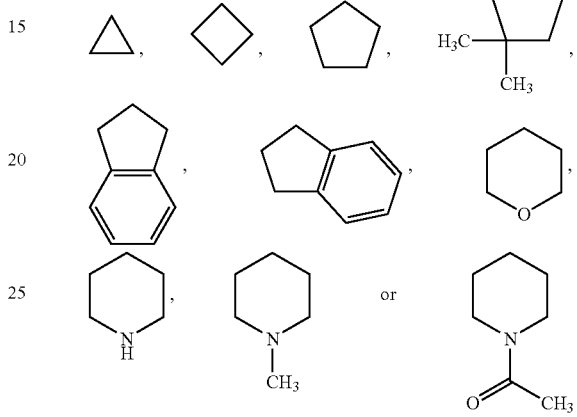

8. A compound according to claim 1 in which R$^2$ represents hydrogen.

9. A compound according to claim 1 in which R$^6$ represents a straight or branched C$_{1-6}$ alkylene chain.

10. A compound according to claim 9 in which R$^6$ represents methylene.

11. A compound according to claim 1 in which L$^2$ is methylene.

12. A compound according to claim 1 in which R$^{12}$ represents hydrogen, halo, C$_{1-4}$ alkyl, or C$_{1-4}$ alkoxy.

13. A compound according to claim 1 in which R$^3$ is 2-methylphenyl.

14. A compound according to claim 1 in which R$^6$ of the group

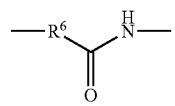

is attached at the ring 6 position.

15. A compound according to claim 1 in which the nitrogen atom of the group

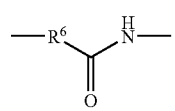

is attached at the ring 4' position.

16. A compound according to claim 1 selected from the group consisting of: (1-{4-[2-(2-o-tolylamino-benzoxazol-6-yl)-acetylamino]-phenyl}-cyclopentyl)-acetic acid; (2-{4-[2-(2-o-tolylamino-benzoxazol-6-yl)-acetylamino]-phenyl}-indan-2-yl)-acetic acid; (4-(4-{2-[4-methyl-2-o-tolylamino-benzoxazol-6-yl]-acetylamino}-phenyl)-tetrahydro-pyran-4-yl)-acetic acid; (4-{4-[2-(2-o-tolylamino-benzoxazol-6-yl)-acetylamino]-phenyl}-tetrahydro-pyran-4-yl)-acetic acid; (1-{4-[2-(2-o-tolylamino-benzoxazol-6-yl)-acetylamino]-phenyl}-indan-1-yl)-acetic acid; (1-{4-[2-[2-o-tolylamino-benzoxazol-6-yl]-acetylamino]-phenyl}-cyclopropyl)-acetic acid; (1-{4-[2-[2-o-tolylamino-benzoxazol-6-yl]-acetylamino]-phenyl}-cyclobutyl)-acetic acid; and [1-{4-[2-[4-methyl-2-o-tolylamino-benzoxazol-6-yl]-acetylamino]-phenyl}-cyclopentyl]-acetic acid; and the corresponding N-oxides and ester prodrugs of such compounds, and pharmaceutically acceptable salts and solvates of such compounds and their N-oxides and ester prodrugs.

17. A pharmaceutical composition comprising an effective amount of a compound according to claim 1 or a corresponding N-oxide or ester prodrug thereof, or a pharmaceutically acceptable salt or solvate of such a compound or an N-oxide or ester prodrug thereof, in association with a pharmaceutically acceptable carrier or excipient.

18. A method for the treatment of a patient suffering from, asthma comprising administering to said patient an effective amount of a compound according to claim 1 or a corresponding N-oxide or ester prodrug thereof, or a pharmaceutically acceptable salt or solvate of such a compound or an N-oxide or ester prodrug thereof.

19. A method for the treatment of a patient suffering from asthma comprising administering to said patient an effective amount of a composition according to claim 17.

* * * * *